United States Patent
Iwase et al.

(10) Patent No.: US 9,566,393 B2
(45) Date of Patent: *Feb. 14, 2017

(54) INJECTION NEEDLE ASSEMBLY AND DRUG INJECTION DEVICE

(71) Applicant: TERUMO KABUSHIKI KAISHA, Tokyo (JP)

(72) Inventors: Yoichiro Iwase, Kanagawa (JP);
Kazunori Koiwai, Kanagawa (JP);
Tetsuo Tanaka, Kanagawa (JP);
Sayaka Oomori, Kanagawa (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 482 days.

This patent is subject to a terminal disclaimer.

(21) Appl. No.: 14/108,699

(22) Filed: Dec. 17, 2013

(65) Prior Publication Data
US 2014/0107578 A1      Apr. 17, 2014

Related U.S. Application Data

(63) Continuation of application No. 13/145,427, filed as application No. PCT/JP2010/051662 on Jan. 29, 2010, now Pat. No. 8,622,963.

(30) Foreign Application Priority Data

Jan. 30, 2009   (JP) .................. 2009-020758
Feb. 2, 2009    (JP) .................. 2009-021771

(51) Int. Cl.
    A61M 5/00    (2006.01)
    A61M 5/42    (2006.01)
    A61M 5/46    (2006.01)

(52) U.S. Cl.
    CPC ............... *A61M 5/425* (2013.01); *A61M 5/46* (2013.01)

(58) Field of Classification Search
    CPC .......................... A61M 5/46; A61M 5/425
    See application file for complete search history.

(56) References Cited

U.S. PATENT DOCUMENTS

4,222,392 A   9/1980   Brennan
6,200,291 B1  3/2001   Di Pietro
              (Continued)

FOREIGN PATENT DOCUMENTS

EP   1752096 A2   2/2007
JP   2000-37456 A  2/2000
              (Continued)

OTHER PUBLICATIONS

International Search Report (PCT/ISA/210) mailed on Sep. 28, 2010, by the Japanese Patent Office as the International Searching Authority for International Application No. PCT/JP2010/051662.
(Continued)

*Primary Examiner* — Aarti B Berdichevsky
(74) *Attorney, Agent, or Firm* — Buchanan Ingersoll & Rooney PC

(57) ABSTRACT

To securely position a needle tip and a blade face of a needle tube inserted into the skin in a predetermined site of a living body, such as the upper layer of skin, an injection needle assembly includes a needle tube having a needle tip capable of puncturing a living body, a hub holding the needle tube, a stabilizer, and a guide portion. The stabilizer is formed in a tubular shape surrounding the circumference of the needle tube, and an end face is pressed against the skin, and thereby a raised portion of the skin is formed in a tube hole. The guide portion is arranged on the stabilizer, and is adapted to recognize a press-in distance y of the stabilizer to the skin.

22 Claims, 15 Drawing Sheets

(56) References Cited

U.S. PATENT DOCUMENTS

| | | |
|---|---|---|
| 7,014,615 B2 | 3/2006 | Erickson et al. |
| 2002/0045858 A1 | 4/2002 | Alchas |
| 2003/0050602 A1 | 3/2003 | Pettis et al. |
| 2005/0131345 A1 | 6/2005 | Miller |
| 2005/0131346 A1 | 6/2005 | Douglas |
| 2007/0005017 A1 | 1/2007 | Alchas et al. |
| 2007/0038148 A1 | 2/2007 | Mechelke et al. |
| 2007/0118077 A1 | 5/2007 | Clarke et al. |
| 2007/0265575 A1 | 11/2007 | Hillios et al. |
| 2008/0033395 A1 | 2/2008 | Alchas |
| 2008/0045900 A1 | 2/2008 | Alchas et al. |
| 2008/0065130 A1 | 3/2008 | Patel et al. |
| 2010/0030148 A1 | 2/2010 | Alchas et al. |
| 2011/0071494 A1 | 3/2011 | Clarke et al. |
| 2011/0166520 A1 | 7/2011 | Iwase et al. |

FOREIGN PATENT DOCUMENTS

| | | |
|---|---|---|
| JP | 2001-137343 A | 5/2001 |
| WO | WO 2008/022755 A1 | 2/2008 |

OTHER PUBLICATIONS

Richard T. Kenney et al., Dose Sparing with Intradermal Injection of Influenza Vaccine, The New England Journal of Medicine, Nov. 25, 2004, pp. 2295-2301.

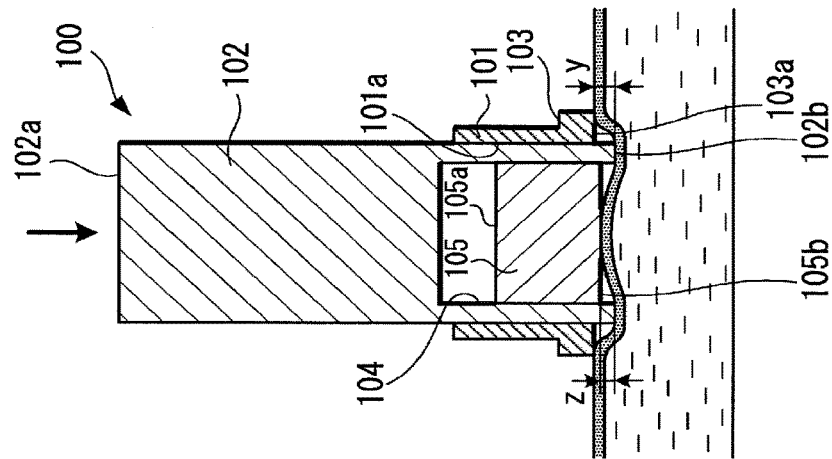
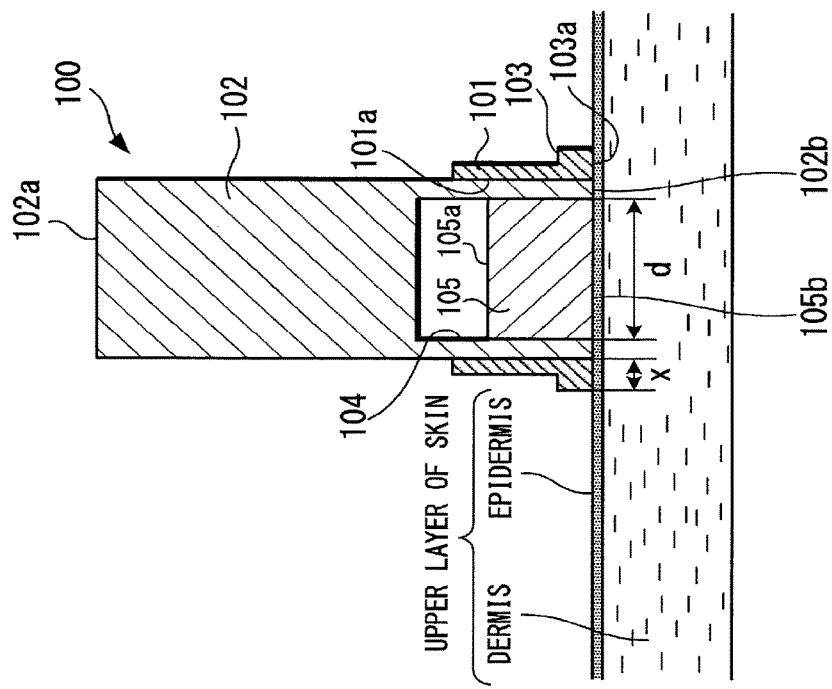

INJECTION NEEDLE ASSEMBLY AND DRUG INJECTION DEVICE

This application is a Continuation of U.S. patent application Ser. No. 13/145,427, filed on Jul. 20, 2011, now U.S. Pat. No. 8,622,963 B2, which is the National Stage of PCT/JP2010/051662, filed on Jan. 29, 2010, and claims priority under 35 U.S.C. §119 to Japanese Patent Application 2009-020758, filed on Jan. 30, 2009, and Japanese Patent Application 2009-021771, filed on Feb. 2, 2009, the entire contents of each of which are incorporated herein by reference.

TECHNICAL FIELD

The present invention relates to an injection needle assembly and a drug injection device used for inserting a needle tip into skin surface to inject a drug into the upper layer of skin.

BACKGROUND ART

Recently, human infection of avian influenza (bird flu) has been reported, and there is a concern about heavy damage caused by widespread human-to-human transmission of bird flu (pandemic). Because of this situation, pre-pandemic vaccine, which is possibly effective against bird flu, is being stockpiled worldwide. Further, to administer the pre-pandemic vaccine to many people, studies are being carried out on increasing the production of vaccine.

Skin is composed of three parts: epidermis, dermis and subcutaneous tissue. The epidermis is a layer of about 50-200 μm from the skin surface, and the dermis is a layer of about 1.5-3.5 mm continuing from the epidermis. Since influenza vaccine is generally subcutaneously or intramuscularly administered, it is administered to the lower layer of skin or a portion deeper than that.

On the other hand, it has been reported that by administering influenza vaccine to the upper layer of skin as a target site where many immunocompetent cells are present, the same immunity acquisition ability as in subcutaneous administration or intramuscular administration can be obtained even with a reduced dosage (Non-patent Document 1). Thus, by administering bird flu vaccine to the upper layer of skin, the dosage can be reduced, so that there is a possibility that bird flu vaccine can be administered to more people. Incidentally, the upper layer of skin refers to the epidermis and dermis of skin.

As the means of administering a drug to the upper layer of skin, methods have been reported such as using a single-needle, a multi-needle, a patch, gas and the like. Considering the stability and reliability of administration and production cost, the method of using a single needle is the most suitable means of administering a drug to the upper layer of skin. As the method of administering vaccine to the upper layer of skin using a single needle, the Mantoux method has been known for a long time. In the Mantoux method, a needle of generally 26-27 G in size having a short bevel needle tip is inserted into the skin about 2-5 mm, from an oblique direction of about 10-15° relative to the skin, to administer a drug of about 100 μL.

However, the Mantoux method is difficult to manipulate and is affected by the skill of the doctor who gives the injection. In particular, it is difficult to administer flu vaccine to a child with the Mantoux method because the child may move during the administration. Accordingly, it is desired to develop a device that can administer vaccine to the upper layer of skin in a simple and convenient manner.

Patent Document 1 describes an injection device for administering a drug to the upper layer of skin. In the injection device, a limiter having a skin contacting surface is connected to a needle hub. The limiter of the injection device described in Patent Document 1 is formed in a tubular shape covering the circumference of a needle tube, and has a gap with the needle tube. By defining the length (protruding length) of the needle tube protruding from the surface of the limiter contacting the skin as a range of 0.5-3.0 mm, the drug is administered in the skin.

Further, Patent Document 2 describes a puncturing adjustment tool for injection needle adapted to prevent the injection needle from puncturing the skin deeper than a target depth. The puncturing adjustment tool for injection needle described in Patent Document 2 includes the one formed in a tubular shape covered around a injection needle, and has a gap with the injection needle. Further, the tubular puncturing adjustment tool for injection needle described includes the one in which the needle tip of the injection needle is formed in a position not protruding from the end portion. When strongly pressing such a puncturing adjustment tool for injection needle against the skin, the skin inside the puncturing adjustment tool for injection needle is raised, and thereby the injection needle is inserted into the skin. Further, the puncturing adjustment tool for injection needle disclosed in Patent Document 2 includes the one which closely contacts the circumference of a needle tube.

Patent Document 1: Japanese Laid-open Patent Application Publication No. 2001-137343
Patent Document 2: Japanese Laid-open Patent Application Publication No. 2000-037456
Non-patent Document 1: R. T. Kenney et al. New England Journal of Medicine, 351, 2295-2301 (2004)

DISCLOSURE OF THE INVENTION

Problems to be Solved by the Invention

However, since the injection device described in Patent Document 1 includes the limiter having the skin contacting surface around the needle tube, and a space of a predetermined size is provided between the limiter and the circumference of the needle tube. Therefore, if the limiter is pressed against skin, the skin will be raised in the space between the limiter and the circumference of the needle tube.

The thickness of the upper layer of skin (epidermis and dermis) differs depending on administration sites, gender differences, races, and ages, however, the depth from the skin surface is in the range of about 0.5-3.0 mm. Further, it is described in Patent Document 1 that the most preferable protruding length of a needle (length protruding from the skin contacting surface of the limiter) is 1.5 mm. On the other hand, it has been reported that the upper layer of skin overlying the deltoid muscle, which is a common vaccine administration site, is about 1.5 mm in thickness in the case of a person having thin skin. Consequently, if the skin is raised in the space between the limiter and the circumference of the needle tube, there is a concern that the tip end of the needle tube may reach the subcutaneous tissue.

Since the epidermis and dermis are composed of dense fibrillar connective tissue and are harder than the subcutaneous tissue, if the tip end of a needle tube reaches the subcutaneous tissue, the administered drug such as vaccine or the like will move from the dermis tissue to the subcutaneous tissue, and therefore the expected effects cannot be obtained.

On the other hand, in the puncturing adjustment tool for injection needle described in Patent Document 2, the height of the raised portion of the skin inside the puncturing adjustment tool for injection needle is equal to the insertion depth of the injection needle. Since the raised portion of the skin formed inside the puncturing adjustment tool for injection needle varies depending on the pressing force exerted when pressing the puncturing adjustment tool for injection needle against the skin, it is difficult to constantly position the needle tip and blade face of the injection needle inserted into the skin in the upper layer of skin.

Further, in the injection devices described in Patent Document 1 and Patent Document 2, due to the provision of the limiter arranged around the needle tube and the puncturing adjustment tool for injection needle closely contacting the circumference of a needle tube, the needle tip of the needle tube is hard to see. Therefore, with the techniques described in Document 1 and Patent Document 2, it is difficult for the user to recognize how much pressing force is being applied to stick the needle tube into the living body. Further, due to unable to recognize a suitable pressing force of the injection device against the living body, it gives the user an uneasy feeling of not knowing whether the needle tip and blade face of the injection needle is securely positioned in the upper layer of skin.

The present invention has been made in view of the above problems, and it is an object of the present invention to securely position the needle tip and blade face of the injection needle inserted into the skin in a predetermined site of the living body, such as the upper layer of skin.

Means for Solving the Problems

To solve the above problems and achieve the object of the present invention, an injection needle assembly according to an aspect of the present invention includes: a needle tube having a needle tip capable of puncturing a living body, a hub for holding the needle tube, a stabilizer, and a guide portion. The stabilizer is formed in a tubular shape surrounding the circumference of the needle tube and has an end face that contacts the skin of the living body when puncturing the living body with the needle tube. The guide portion is provided on the stabilizer for guiding, by being contacted with the skin, a pressing parameter applied from the needle tube and the stabilizer to the living body when puncturing the living body with the needle tube.

a drug injection device according to another aspect of the present invention includes: a needle tube having a needle tip capable of puncturing a living body, a hub for holding the needle tube, a syringe connected to the hub, a stabilizer, and a guide portion. The stabilizer is formed in a tubular shape surrounding the circumference of the needle tube and has an end face that contacts the skin of the living body when puncturing the living body with the needle tube. The guide portion is provided on the stabilizer for guiding, by being contacted with the skin, a pressing parameter applied from the needle tube and the stabilizer to the living body when puncturing the living body with the needle tube.

Incidentally, "guiding a pressing parameter" means guiding or recognizing the pressing parameter for pressing the needle tube and the stabilizer against the living body when puncturing the living body with the needle tube so that the pressing parameter becomes a predetermined value.

Further, the stabilizer of the injection needle assembly of the present invention is a skin deformer adapted to form a raised portion of the skin in a tube hole thereof by pressing the end face of the stabilizer against the skin. Further, the pressing parameter refers to a press-in distance of the skin deformer into the skin, and the guide portion is a distance recognizer adapted to recognize the press-in distance.

In the injection needle assembly, the press-in distance of the skin deformer into the skin can be recognized by the distance recognizer. Thus, when the end face of the skin deformer is pressed against the skin, the press-in distance of the skin becomes constant, and therefore the height of the raised portion of the skin formed in tube hole of the skin deformer can be made constant. The needle tube is stuck into the raised portion of the skin.

Further, the injection needle assembly further includes an adjusting portion arranged around the needle tube, the adjusting portion having a needle-protruding surface from which the needle tip of the needle tube protrudes. Further, the size of the needle tube is 26-33 G, and the pressing parameter refers to a pressing force.

Advantages of the Invention

With the injection needle assembly and the drug injection device according to the present invention, due to the provision of the guide portion for guiding the pressing parameter when puncturing the living body, the needle tip and the blade face of the needle tube can be securely positioned in the upper layer of skin.

With the injection needle assembly and the drug injection device according to the present invention, the height of the raised portion of the skin formed by the skin deformer can be made constant, and the needle tip and the blade face of the needle tube can be securely positioned in the upper layer of skin.

Further, with the injection needle assembly and the drug injection device according to the present invention, the pressing force applied from the needle tube and the stabilizer to the living body can be guided to the user by the guide portion, and therefore the user can stick the needle tube into the skin with ensuring a suitable predetermined pressing force. Further, since being able to recognize the suitable pressing force applied from the needle tube and the stabilizer to the living body, the user can use the drug injection device without uneasy feeling, and the needle tip and the blade face of the needle tube can be securely positioned in the upper layer of skin.

BRIEF DESCRIPTION OF DRAWINGS

FIGS. 4A and 4B are views showing a measuring device for measuring a height of a raised portion of the skin and a distance corresponding to a recognizer height formed in a tube by a skin deformer of the injection needle assembly according to the first embodiment of the present invention.

FIG. 15A is a view showing a state where the measuring device is mounted on the skin, and FIG. 15B is a view showing a state where a pressing member of the measuring device is pressed.

BEST MODES FOR CARRYING OUT THE INVENTION

Figure 1:
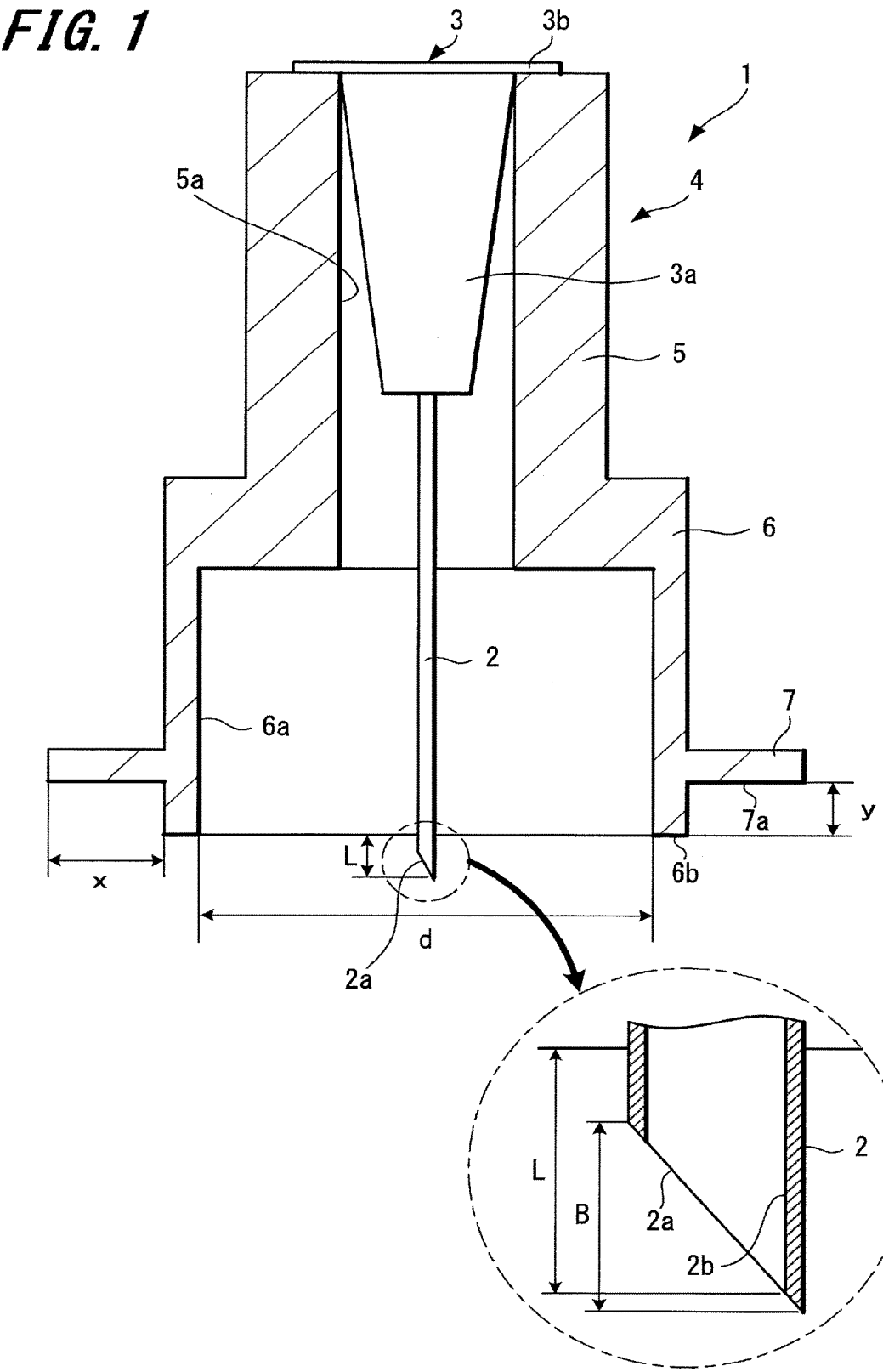
FIG. 1 is a view showing the configuration of an injection needle assembly according to a first embodiment of the present invention.

Embodiments of an injection needle assembly and a drug injection device according to the present invention will be described below with reference to FIGS. 1 to 18. Note that, in the drawings, common components are denoted by common numerals. Further, the present invention is not limited to the embodiments described below.

1. First Embodiment

Configuration Examples of Injection Needle Assembly and Drug Injection Device

Figure 2:
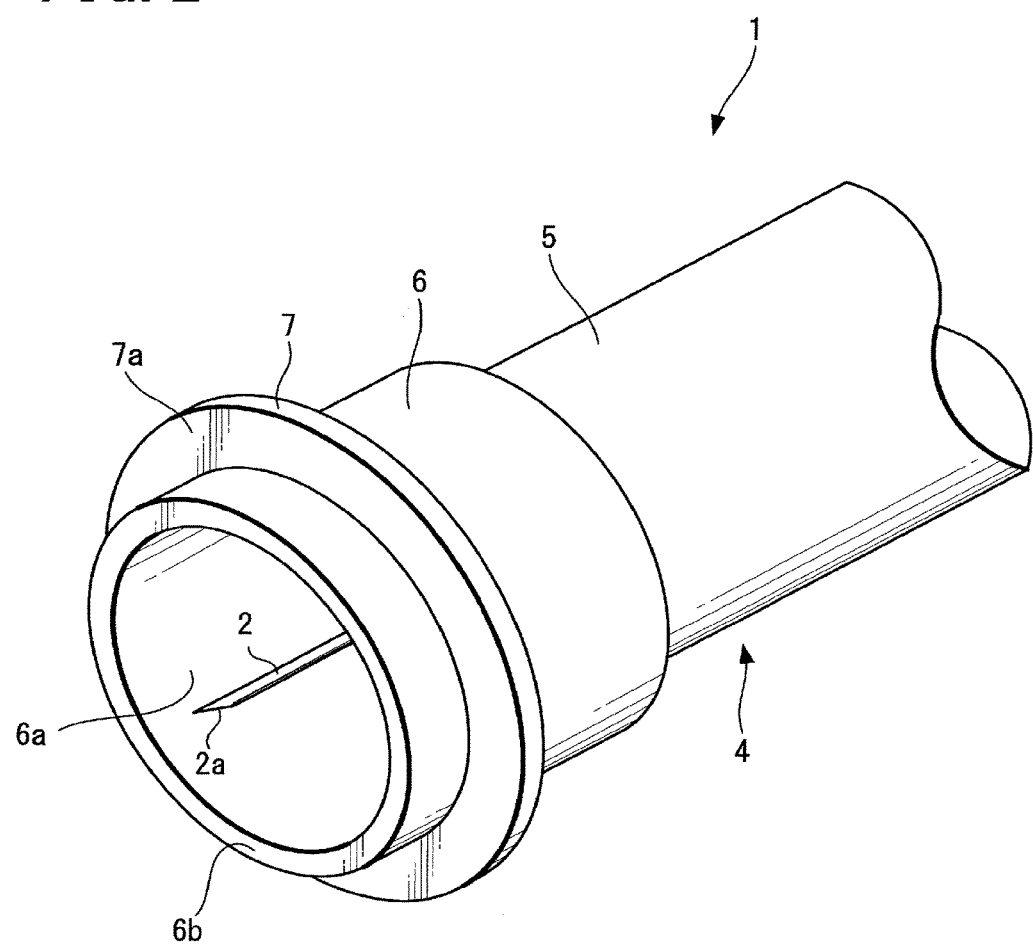
FIG. 2 is a perspective view showing the injection needle assembly according to the first embodiment of the present invention.
Figure 3:
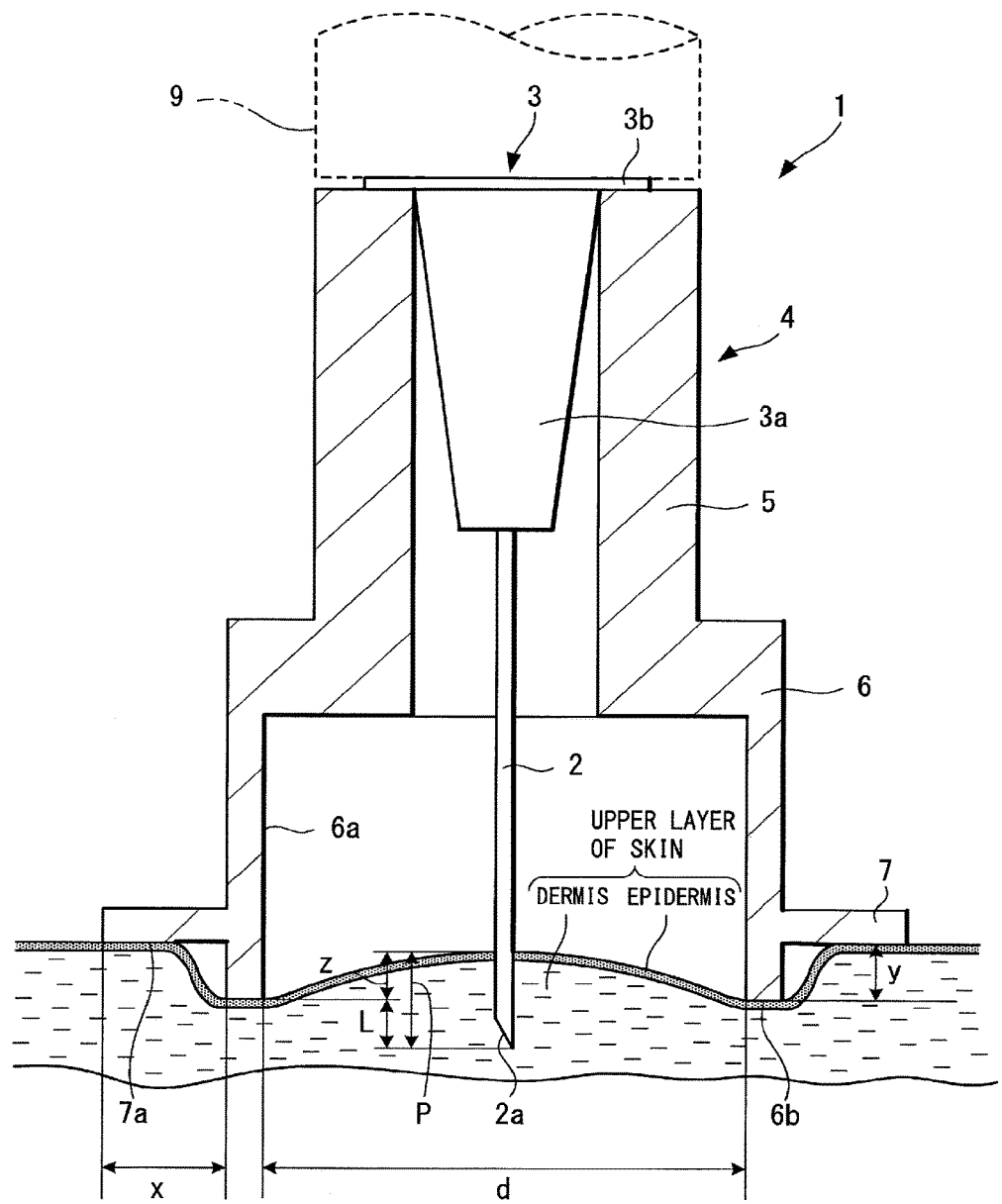
FIG. 3 is a view for explaining a state in which a needle tube of a drug injection device according to the first embodiment of the present invention is stuck into the skin.

An injection needle assembly and a drug injection device according to a first embodiment of the present invention will be described below with reference to FIGS. 1 to 3.

FIG. 1 is a view showing the configuration of the injection needle assembly according to the first embodiment of the present invention. FIG. 2 is a perspective view showing the injection needle assembly according to the first embodiment of the present invention. FIG. 3 is a view for explaining a state in which a needle tube of the injection needle assembly of the drug injection device is stuck into the skin.

An injection needle assembly 1 includes a hollow needle tube 2 having a needle hole 2b, a hub 3 which holds the needle tube 2, and a stabilizer (which is a skin deformer) 4 fixed to the hub 3. A drug injection device of the present invention is configured by connecting a syringe 9 (see FIG. 3) with the hub 3 of the injection needle assembly 1.

A needle tube of 26-33 G (external diameter: 0.2-0.45 mm), preferably 30-33 G, in size according to ISO standard for medical needle tubes (ISO9626: 1991/Amd. 1:2001(E)) is used as the needle tube 2. A blade face 2a is formed in the tip end portion of the needle tube 2 so that the needle tip is acute-angled. The length of the blade face 2a in the direction in which the needle tube 2 extends (referred to as "bevel length B" hereinafter) may be equal to or less than 1.4 mm (which is the minimum thickness of the upper layer of skin of an adult, which is to be described later), but equal to or greater than about 0.5 mm, which is the bevel length when a short bevel is formed in a needle tube of 33 G. In other words, it is preferred that the bevel length B is set in a range of 0.5-1.4 mm.

Additionally, it is further preferred that the bevel length B is equal to or less than 0.9 mm (which is the minimum thickness of the upper layer of skin of a child). Namely, it is further preferred that the bevel length B is set in a range of 0.5-0.9 mm. Incidentally, the short bevel refers to a blade face forming an angle of 18-25° with respect to the longitudinal direction of the needle, which is generally used as an injection needle.

The material of the needle tube 2 may be, for example, stainless steel, aluminum, aluminum alloy, titanium, titanium alloy, and other metals. Further, the needle tube 2 may be a straight needle, a tapered needle in which at least a portion thereof is tapered, or the like. The tapered needle may have a configuration in which the external diameter of a base end portion fixed to the hub 3 is larger than the external diameter of a tip end portion including the needle tip, and a middle portion is tapered.

The needle hole 2b of the needle tube 2 is communicated with the hub 3. The hub 3 includes a hub body 3a which holds the needle tube 2, and a flange 3b formed continuously from the hub body 3a. The hub body 3a has a tapered structure whose diameter becomes smaller gradually toward the tip end thereof. The base end portion of the needle tube 2 is fixed to the tip end portion of the hub body 3a. The flange 3b is formed in the base end portion of the hub body 3a. A stabilizer 4 abuts on the flange 3b so as to be fixed to the flange 3b. The hub 3 may be in any form as long as it can be connected with the syringe.

The syringe 9 may be either the one that is filled with a drug when using the drug injection device or a pre-filled syringe that is filled with a drug in advance. Examples of the drug filled in the syringe 9 include vaccines. However drugs using macromolecular substance, such as cytokine or the like, and hormones may also be filled in the syringe 9.

The stabilizer 4 has a shape in which two circular tubes different in diameter are continuous in the axial direction. The stabilizer 4 includes a fixing portion 5 and a contact portion 6 continuously formed with fixing portion 5, the former forming one end portion of the stabilizer 4, and the latter forming the other end portion of the stabilizer 4. The material of the stabilizer 4 may be either a synthetic resin (plastic) such as polycarbonate, polypropylene, polyethylene or the like, or a metal such as stainless steel, aluminum or the like.

The fixing portion 5 of the stabilizer 4 is formed by a circular tube having a tube hole 5*a*. One end of the fixing portion 5 is continuous with the contact portion 6. Further, the other end of the fixing portion 5 is fixed to the flange 3*b* of the hub 3 by a fixing means such as an adhesive. Further, the hub body 3*a* of the hub 3 is housed in the tube hole 5*a* of the fixing portion 5.

The contact portion 6 of the stabilizer 4 is formed by a circular tube having a diameter larger than that of the fixing portion 5, and has a tube hole 6*a* communicating with the tube hole 5*a* of the fixing portion 5. The diameter of the tube hole 6*a* of the contact portion 6 is larger than that of the tube hole 5*a* of the fixing portion 5. The needle tube 2 held by the hub 3 is arranged in the tube hole 6*a* of the contact portion 6. Further, the central line of the tube hole 6*a* coincides with the axis of the needle tube 2.

When puncturing the upper layer of skin with the needle tube 2, an end face 6*b* of the contact portion 6 is brought into contact with and pressed against the surface of the skin. When the end face 6*b* of the contact portion 6 is pressed against the skin, a raised portion of the skin is formed in the tube hole 6*a* of the contact portion 6. In other words, the stabilizer 4 has a function as a skin deformer for deforming the skin. Further, the needle tube 2 is stuck into the raised portion of the skin formed in the tube hole 6*a*.

A guide portion (which is a distance recognizer) 7 is formed integrally with the outer circumferential surface of the contact portion 6. The guide portion 7 projects from the contact portion 6 in the radial direction to form a circular ring shape continuing in the circumferential direction of the contact portion 6. In other words, the guide portion 7 is a flange projecting from the outer circumferential surface of the contact portion 6. The guide portion 7 has a contact surface 7*a* parallel to the end face 6*b* of the contact portion 6. By pressing the contact portion 6 until the contact surface 7*a* contacts the skin, the press-in distance of the contact portion 6 to the skin can always be made constant. In other words, the guide portion 7 has a function for recognizing the press-in distance of the contact portion 6 to the skin.

As a result, the height of the raised portion of the skin formed in the tube hole 6*a* of the contact portion 6 can be made substantially constant. The insertion depth of the needle tube 2 into the skin is equal to the sum of the height of the raised portion of the skin and the distance from the end face 6*b* of the contact portion 6 to the needle tip of the needle tube 2. Thus, by making the height of the raised portion of the skin substantially constant, the insertion depth of the needle tube 2 into the skin can be made constant.

In the present embodiment, the stabilizer 4 and the guide portion 7 are integrally formed with each other. However, the distance recognizer of the present invention may also be formed separately from the skin deformer. In such case, the guide portion (the distance recognizer) is fixed to the skin deformer by a fixing means such as a screw, an adhesive or the like.

The distance between the end face 6*b* of the contact portion 6 and the tip end of the needle hole 2*b* of the needle tube 2 is referred to as "needle-protruding length L" hereinafter. Further, the height of the raised portion of the skin from the end face 6*b* is referred to as "skin-raising length z" (see FIG. 3), and the sum of the needle-protruding length L and the skin-raising length z is referred to as "insertion length P" hereinafter. Further, the length of the contact surface 7*a* of the guide portion 7 in the direction perpendicular to the outer circumferential surface of the contact portion 6 is referred to as "guide portion length (recognizer length) x", and the distance between the end face 6*b* of the contact portion 6 and the contact surface 7*a* of the guide portion 7 is referred to as "guide portion height (recognizer height) y" hereinafter.

The guide portion length x is also a projected length of the guide portion 7 from the contact portion 6. The guide portion length x is set considering the guide portion height y. This is because, if the guide portion length x is not increased in proportion to the increase of the guide portion height y, the press-in distance of the end face 6*b* of the contact portion 6 to the skin will increase.

The needle-protruding length L becomes a positive value when the needle tip of the needle tube 2 projects from the end face 6*b* of the contact portion 6, and the needle-protruding length L becomes a negative value when the needle tip of the needle tube 2 is located in the tube hole 6*a* of the contact portion 6. The needle-protruding length L can be suitably set by changing the length of the needle tube 2, and/or changing the length of the hub 3 which holds the needle tube 2, or the like. In order to reduce the risk of unexpected needle-stick accident, it is preferred that the needle tip of the needle tube 2 does not project from the end face 6*b*.

The needle-protruding length L is determined based on the insertion length P and the skin-raising length z ($L=P-z$). The insertion length P is set within the range of the thickness of the upper layer of skin. On the other hand, by performing the below-mentioned experiments, it is made known that the skin-raising length z varies with the variations of the guide portion length x and the guide portion height y. Thus, the needle-protruding length L can be determined by setting the skin-raising length z based on the guide portion length x and the guide portion height y.

Herein, the thickness of the upper layer of skin will be described below. As described above, the upper layer of skin means the epidermis and the dermis of the skin. The thickness of the upper layer of skin is generally in a range of 0.5-3.0 mm. Therefore, the insertion length P may be set in a range of 0.5-3.0 mm.

Generally, the influenza vaccine administration site is deltoid muscle. Therefore, the thickness of the upper layer of skin overlying the deltoid muscle was measured for 19 children and 31 adults. The measurements were performed by imaging the upper layer of skin having high ultrasonic reflectivity using an ultrasonic measurement device (NP60R-UBM High Resolution Echo for Small Animal, NEPA GENE, CO., LTD.). Incidentally, since the measured values showed lognormal distribution, the range of MEAN±2SD was obtained by taking the geometrical mean.

The results showed that the thickness of the upper layer of skin overlying the deltoid muscle of a child was 0.9-1.6 mm. Further, the results also showed that the thickness of the upper layer of skin overlying the deltoid muscle of an adult was 1.4-2.6 mm in the distal part, 1.4-2.5 mm in the middle part, and 1.5-2.5 mm in the proximal part. It can be confirmed from the above that the thickness of the upper layer of skin overlying the deltoid muscle is equal to or more than 0.9 mm for children, and is equal to or more than 1.4 mm for adults. Consequently, when performing an injection on the upper layer of skin overlying the deltoid muscle, it is preferred that the insertion length P is set in a range of 0.9-1.4 mm as the maximum.

Further, by setting the insertion length P in this manner, it becomes possible to securely position the blade face 2a in the upper layer of skin. As a result, the needle hole (the drug solution outlet) 2b opening in the blade face 2a can be positioned in the upper layer of skin, regardless of its position in the blade face 2a. Incidentally, even when the drug solution outlet is positioned in the upper layer of skin, if the needle tip is inserted into a depth deeper than the upper layer of skin, the drug solution will flow into the subcutaneous tissue from between the side faces of the end portion of the needle tip and the incised skin, and therefore it is important that the needle tip and blade face of the needle tube 2 are securely positioned in the upper layer of skin.

Incidentally, although it is preferred that the bevel portion is positioned in the skin when being inserted, however, if the size of the needle tube is larger than 26 G, it will be difficult to make the bevel length B 1.0 mm or less. Accordingly, it is preferred that a needle tube smaller than 26 G is used in order to set the insertion length P in the preferable range (0.9-1.4 mm).

Next, the diameter of the tube hole 6a of the contact portion 6 will be described below. The diameter of the tube hole 6a is referred to as "internal diameter d" hereinafter.

Generally, when a drug solution of about 100 μL is injected into the upper layer of skin, a blister of about 9-12 mm in diameter will be formed in the skin. Thus, in order for the stabilizer 4 to not obstruct the formation of the blister, it is preferred that the internal diameter d is set to 12 mm or greater, which is the size that does not obstruct the formation of the blister when the contact portion 6 is pressed against the skin to administer the drug. However, the blister can be formed in the tube hole 6a even the internal diameter d is set to 8 mm, which is smaller than the diameter of the blister, and the administration of the drug is possible. Incidentally, no upper limit is particularly set for the internal diameter d as long as the internal diameter d is equal to 8 mm or greater. However, if the internal diameter d is set too large, both the external diameter of the stabilizer and the external diameter of the guide portion 7 will be large.

If the external diameter of the stabilizer 4 and the external diameter of the guide portion 7 are large, when the needle tube 2 is to be stuck into an arm, for example, it will be difficult to bring the guide portion 7 into contact with the skin. Thus, considering the slender arms of children, it is preferred that the external diameter of the guide portion 7 is set to about 30 mm as the maximum. Here, if the width of the end face of the contact portion 6 is 0.5 mm and the guide portion length x is 0.5 mm, which is considered as the minimum, the internal diameter d will be 28 mm as the maximum.

The external diameter of the guide portion 7 is determined based on the width of the end face of the contact portion 6, the internal diameter d, and the guide portion length x. In the present embodiment, the width of the end face of the contact portion 6 is set to 0.5 mm. Further, the internal diameter d is set in a range of 11-14 mm, and the guide portion length x is set in a range of 0.5-6.0 mm. Thus, the external diameter of the guide portion 7 is in a range of 13-27 mm, and therefore the contact surface 7a of the guide portion 7 can be brought into contact with the skin.

Method of Using Drug Injection Device

Next, a method of using the drug injection device to which the injection needle assembly 1 is applied will be described below with reference to FIG. 3.

First, the end face 6b of the contact portion 6 of the stabilizer 4 is caused to face the skin, and thereby the needle tip of the needle tube 2 is caused to face the skin to be punctured. Next, the drug injection device is moved substantially perpendicular to the skin, and the end face 6b of the contact portion 6 is pressed against the skin.

At this time, if the needle tip of the needle tube 2 projects from the end face 6b of the contact portion 6, the needle tip will touch the skin first before the end face 6b is brought into contact with the skin, however, instead of being immediately penetrated by the needle tube 2, the skin is slightly recessed due to being pressed by the needle tube 2. While if the needle tip of the needle tube 2 is located in the tube hole 6a of the contact portion 6, the needle tip of the needle tube 2 will touch the skin after the end face 6b of the contact portion 6 is brought into contact with the skin.

Further, when the end face 6b of the contact portion 6 is pressed against the skin, a raised portion of the skin is formed in the tube hole 6a of the contact portion 6. In other words, the skin to be punctured by the needle tube 2 is raised. At this time, the needle tip of the needle tube 2 is stuck into the skin. Further, when the contact portion 6 is pressed until the guide portion 7 touches the skin, the press-in distance of the skin by the contact portion 6 reaches a predetermined value. Thus, by bringing the guide portion 7 into contact with the skin, the press-in distance of the contact portion 6 to the skin can always be made constant, and therefore the skin-raising length z can be made substantially constant. Here, the press-in distance of the skin is defined as one of the pressing parameters when puncturing the skin.

By making skin-raising length z substantially constant, the insertion depth of the needle tube 2 into the skin can be made substantially constant. Thus, if the needle-protruding length L is set considering the skin-raising length z, both the needle tip of the needle tube 2 and the tip end of the needle hole 2b can be securely positioned in the upper layer of skin. For example, when the skin-raising length z is set to 0.8 mm, the needle-protruding length L is set to 0.4 mm. As a result, the insertion length P becomes 1.2 mm, and therefore the tip end of the needle hole 2b of the needle tube 2 can be positioned within the range of the thickness of the upper layer of skin.

Thereafter, the drug solution is discharged from the needle hole 2b of the needle tube 2 by operating the syringe 9 connected to the hub 3. As a result, the drug solution is injected into the upper layer of skin.

Experimental Examples

Next, experimental examples in which the height of the raised portion of the skin formed in the tube hole 6a of the contact portion 6 (i.e., the skin-raising length z) and the press-in distance of the contact portion 6 to the skin (corresponding to the guide portion height y) were measured will be described below with reference to FIGS. 4A to 9.

Figure 5:
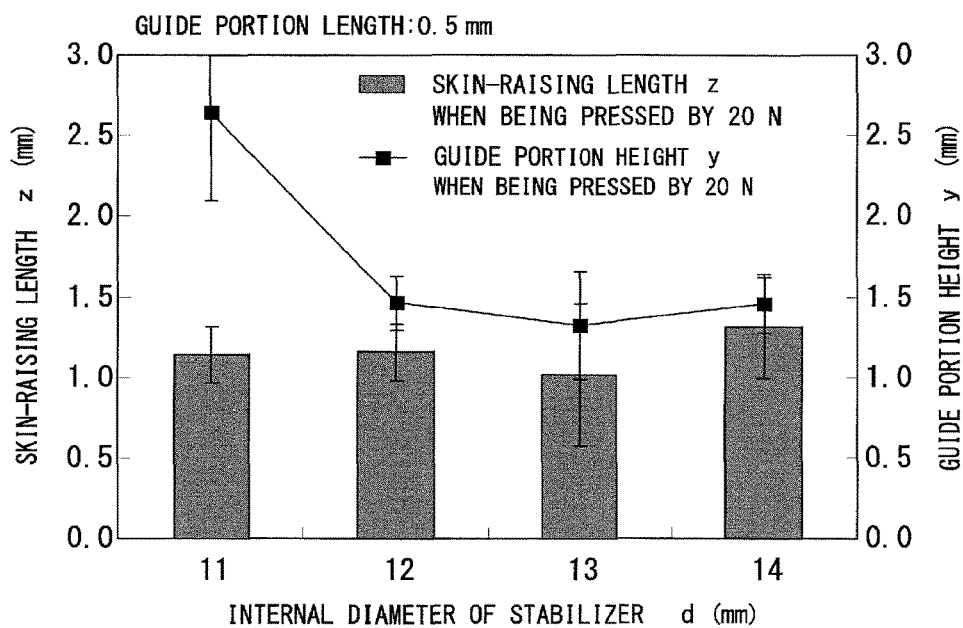
FIG. 5 is a graph showing the height of the raised portion of the skin (skin-raising length) and the distance corresponding to the recognizer height (moving distance of an outer tube) measured using the measuring device shown in FIGS. 4A and 4B, the measured values being obtained by varying the diameter of a tube hole of the skin deformer.
Figure 6:
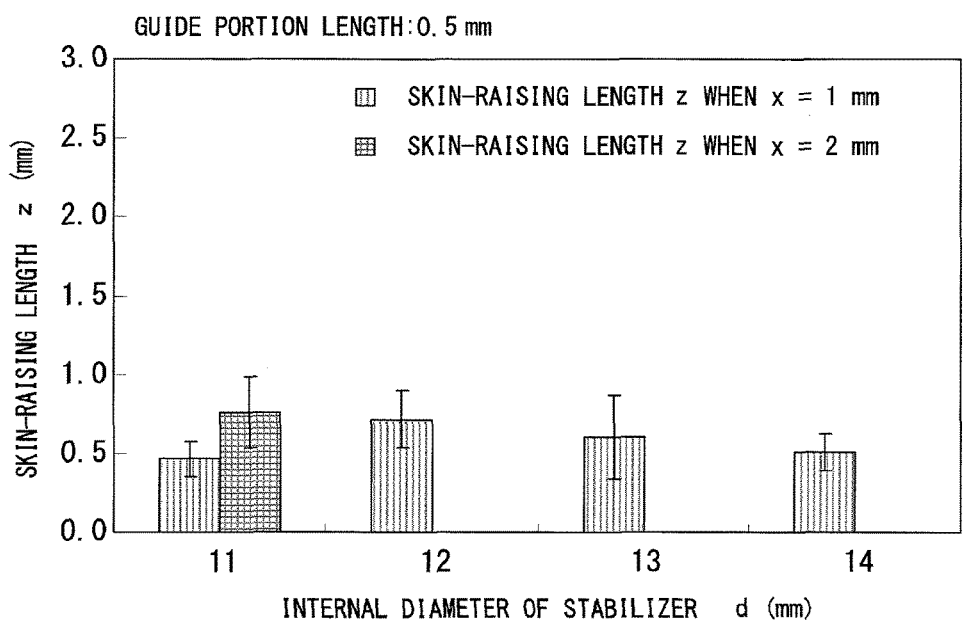
FIG. 6 is a graph showing the height of the raised portion of the skin measured using the measuring device shown in FIGS. 4A and 4B, the measured values being obtained by varying the diameter of the tube hole of the skin deformer and the distance corresponding to the recognizer height (the moving distance of the outer tube).
Figure 7:
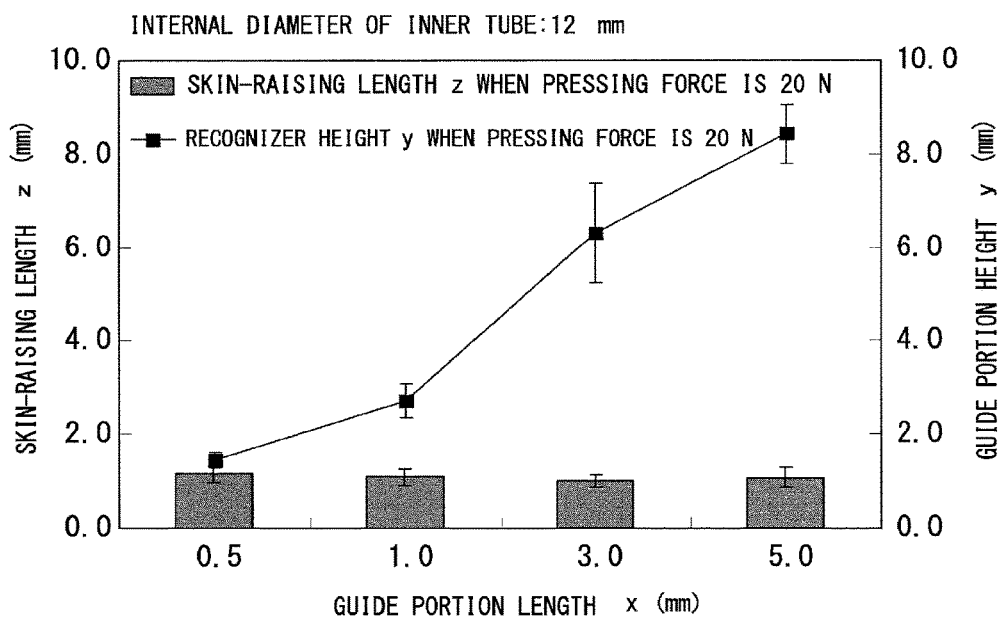
FIG. 7 is a graph showing the height of the raised portion of the skin and the distance corresponding to the recognizer height (the moving distance of the outer tube) measured using the measuring device shown in FIGS. 4A and 4B, the measured values being obtained by varying the recognizer length.
Figure 8:
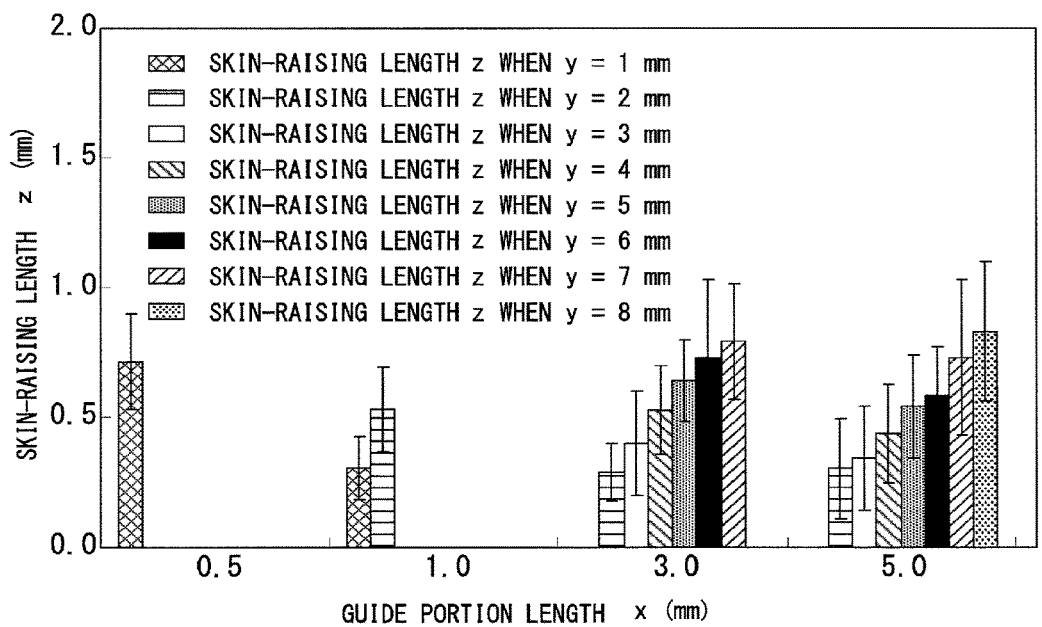
FIG. 8 is a graph showing the height of the raised portion of the skin measured using the measuring device shown in FIGS. 4A and 4B, the measured values being obtained by varying the recognizer length and the moving distance of the outer tube corresponding to the recognizer height.
Figure 9:
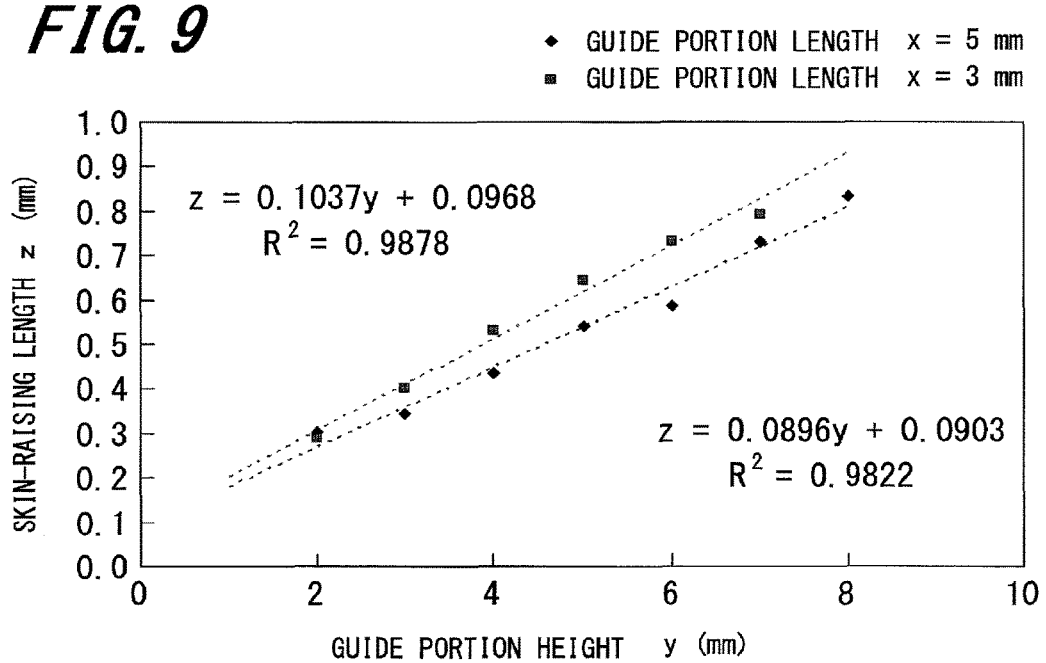
FIG. 9 is a graph showing the relation between the recognizer height and the height of the raised portion of the skin.

FIGS. 4A and 4B are views showing a measuring device for measuring the skin-raising length z and the guide portion height y. FIG. 5 is a graph showing the measured values of the skin-raising length z and the guide portion height y obtained by varying the internal diameter d. FIG. 6 is a graph showing the measured value of the skin-raising length z obtained by varying the guide portion height y and the internal diameter d. FIG. 7 is a graph showing the height of the raised portion of the skin (the skin-raising length z) and the distance (the moving distance of the outer tube) corresponding to the recognizer height (the guide portion height y) measured using the measuring device shown in FIGS. 4A and 4B, the measured values being obtained by varying the recognizer length (the guide portion length x). FIG. 8 is a graph showing the height of the raised portion of the skin measured using the measuring device shown in FIGS. 4A and 4B, the measured values being obtained by varying the recognizer length and the moving distance of the outer tube corresponding to the recognizer height. FIG. 9 is a graph showing the relation between the recognizer height and the height of the raised portion of the skin.

First, a measuring device 100 used in this experiment will be described below. The measuring device 100 is formed by cutting a synthetic resin (plastic). The measuring device 100 includes an outer tube 101 formed in a circular tube shape, and a pressing member 102 fitted into the outer tube 101 in a manner in which the pressing member 102 can be slid against a tube hole 101a of the outer tube 101.

A flange 103 projecting in the radial direction of the outer tube 101 is provided on one end portion (a lower end portion) of the outer tube 101. A bottom surface 103a of the flange 103 is coplanar with an end face of the outer tube 101. The flange 103 corresponds to the guide portion 7 of the injection needle assembly 1 (see FIG. 1). Further, the length between the outer circumferential surface of the flange 103 and the inner surface of the outer tube 101 corresponds to the guide portion length x of the injection needle assembly 1.

The pressing member 102 is formed by a cylinder having substantially the same diameter as the diameter of the tube hole 101a of the outer tube 101, and has an upper surface 102a and a bottom surface 102b. A circular recess 104 is formed in the bottom surface 102b of the pressing member 102. The diameter of the recess 104 corresponds to the internal diameter d of the injection needle assembly 1. A measuring member 105 is slidably fitted into the recess 104. The measuring member 105 is formed by a cylinder having substantially the same diameter as the diameter of the recess 104, and has an upper surface 105a and a bottom surface 105b.

On the other hand, since being provided with the recess 104, the bottom surface 102b of the pressing member 102 is formed in a circular ring shape. The bottom surface 102b of the pressing member 102 corresponds to the end face 6b of the contact portion 6 of the injection needle assembly 1. Incidentally, in the measuring device 100 used in the present experiment, the width of the bottom surface 102b of the pressing member 102 is set to 0.5 mm.

To measure the skin-raising length z and the guide portion height y using the measuring device 100 having the aforesaid configuration, first the measuring device 100 is mounted on the skin as shown in FIG. 4A. At this time, the bottom surface 103a of the flange 103 provided to the outer tube 101, the bottom surface 102b of the pressing member 102, and the bottom surface 105b of the measuring member 105 are brought into contact with the skin.

Next, as shown in FIG. 4B, the upper surface 102a of the pressing member 102 is pressed, and thereby the pressing member 102 is moved relative to the tube hole 101a of the outer tube 101, so that the bottom surface 102b of the pressing member 102 is pressed against the skin. As a result, the outer tube 101 and the pressing member 102 are formed into the same configuration as the stabilizer 4 in the state where the contact portion 6 is pressed against the skin.

When the bottom surface 102b of the pressing member 102 is pressed against the skin, a raised portion of the skin is formed in the recess 104, and thereby the measuring member 105 is pushed up by the raised portion of the skin. In such state, the distance between the bottom surface 102b of the pressing member 102 and the bottom surface 105b of the measuring member 105 corresponds to the height of the raised portion of the skin (the skin-raising length z) caused by the stabilizer 4 of the injection needle assembly 1. Thus, the skin-raising length z can be measured by measuring the distance between the bottom surface 102b of the pressing member 102 and the bottom surface 105b of the measuring member 105.

Further, the distance between the bottom surface 102b of the pressing member 102 and the bottom surface 103a of the flange 103 corresponds to the guide portion height y of the injection needle assembly 1. Thus, the guide portion height y can be measured by measuring the distance between the bottom surface 102b of the pressing member 102 and the bottom surface 103a of the flange 103.

In the present experiment, the skin-raising length z and the guide portion height y of the skin overlying the deltoid muscle were measured for 10 adults. In the present experiment, first the skin-raising length z and the guide portion height y were measured by using four measuring devices 100, wherein the diameters (the internal diameters d) of the recesses 104 of the four measuring devices 100 were 11 mm, 12 mm, 13 mm and 14 mm respectively. Incidentally, the guide portion length x was set to 0.5 mm. The upper limit of the force for pressing the pressing member 102 was set to 20 N, which was considered to be the maximum applicable value in practical use. By performing such a measurement, it is possible to confirm whether or not the skin-raising length z varies with the variation of the internal diameter d. The experimental result is shown in FIG. 5.

As shown in FIG. 5, in the case where a force of 20 N was applied to press the pressing member 102 against the skin, the skin-raising length z was in a range of 1.0-1.3 mm. For example, when the internal diameter d was set to 11 mm, the skin-raising length z was about 1.1 mm. It is understood from the result that, when the internal diameter d varies within a range of 11-14 mm, the skin-raising length z is hardly affected by the variation of the internal diameter d. Further, the guide portion height y was shifted by 2.6 mm when the internal diameter d was set to 11 mm, and shifted by 1.5 mm when the internal diameter d was set in a range of 12-14 mm.

Next, the skin-raising length z was measured for both the cases where the pressing member 102 was pressed until the guide portion height y had reached 1 mm and 2 mm respectively. The results are shown in FIG. 6. In the case where the guide portion height y was 1 mm, the skin-raising length z was within a range of 0.5-0.7 mm when the internal diameter d was in the range of 11-14 mm. The skin-raising length z reached the largest value of about 0.7 mm when the internal diameter d was 12 mm. Further, in the case where the guide portion height y was 2 mm, the skin-raising length z was about 0.8 mm when internal diameter d was 11 mm.

Next, since the skin-raising length z at a pressing force of 20 N was about 1.2 mm despite variation of the internal diameter d, the internal diameter d was set to 12 mm, and the skin-raising length z and the guide portion height y were measured by varying the guide portion length x in a range of 0.5-5 mm. The experimental result is shown in FIG. 7.

First, the force for pressing the pressing member 102 was set to 20 N, and the skin-raising length z and the guide portion height y were measured. As shown in FIG. 7, when the guide portion length x was increased, the guide portion height y increased. Also, the skin-raising length z was in a range of 1.0-1.2 mm.

Next, the skin-raising length z was measured by varying the guide portion height y in a range of 1-8 mm. The results are shown in FIG. 8. When the guide portion height y was increased, the skin-raising length z increased. Thus, it is understood that the skin-raising length z changes substantially in proportion to the guide portion height y (see FIG. 9). Thus, the skin-raising length z can be set based on the guide portion height y.

FIG. 9 is a graph showing the relation between the guide portion height y and the skin-raising length z (the height of the raised portion of the skin). It is understood from FIG. 9 that, when the guide portion length x is 3 mm, for example, the skin-raising length z and the guide portion height y satisfy the relation defined by the following expression.

$z=0.104y+0.097$ (correlation coefficient 0.99)

Further, when the guide portion length x is 5 mm, the skin-raising length z and the guide portion height y satisfy the relation defined by the following expression.

$z=0.090y+0.090$ (correlation coefficient 0.98)

Incidentally, it can be said that the above two relational expressions have substantially the same constant. In other words, it can be said that, if each constant is rounded off to one decimal place, the skin-raising length z and the guide portion height y satisfy the relation defined by the following expression.

$z=0.1y+0.1$

Thus, the above relational expression can be applied when the guide portion length x is set in a range of 3.0-5.0 mm.

Further, when the guide portion length x was set to 0.5 mm, the guide portion height y could be set to 1 mm, however, the guide portion height y could not be set to 2 mm or higher. In other words, although it was tried to press the pressing member 102 against the skin until the guide portion height y reached 2 mm, the bottom surface 103a of the flange 103 failed to come into contact with the skin. Thus, it is understood that, when the guide portion length x is set to 0.5 mm, the guide portion height y should be set to 1 mm or lower. In the same manner, it is understood that, when the guide portion length x is set to 1.0 mm, the guide portion height y should be set to 2 mm or lower.

It is understood, based on the above experimental results, that the insertion length P (see FIG. 3) can be defined by changing the guide portion height y. For example, if the guide portion length x is set to 0.5 mm and the guide portion height y is set to 1.5 mm, the skin-raising length z will become about 1.2 mm. Thus, if the needle-protruding length L is set to 0.2 mm, the insertion length P can be set to 1.4 (1.2+0.2=1.4) mm, and therefore the tip end of the needle tube 2 can be securely positioned in the upper layer of skin of an adult. Further, if the needle-protruding length L is set to −0.3 mm, the insertion length P can be set to 0.9 (1.2−0.3=0.9) mm, and therefore the tip end of the needle tube 3 can be securely positioned in the upper layer of skin of a child.

Further, when the guide portion length x is in a range of 3.0-5.0 mm and the internal diameter d is in a range of 11-14 mm, the guide portion height y and the skin-raising length z satisfy the relation defined by the relational expression of: $z=0.1y+0.1$. Thus, the skin-raising length z can be defined depending on this relational expression. Further, the needle-protruding length L can be determined based on the defined skin-raising length z and the insertion length P (L=P−z).

2. Second Embodiment

Configuration Examples of Injection Needle Assembly and Drug Injection Device An injection needle assembly and a drug injection device according to a second embodiment of the present invention will be described below with reference to FIG. 10.

Figure 10:
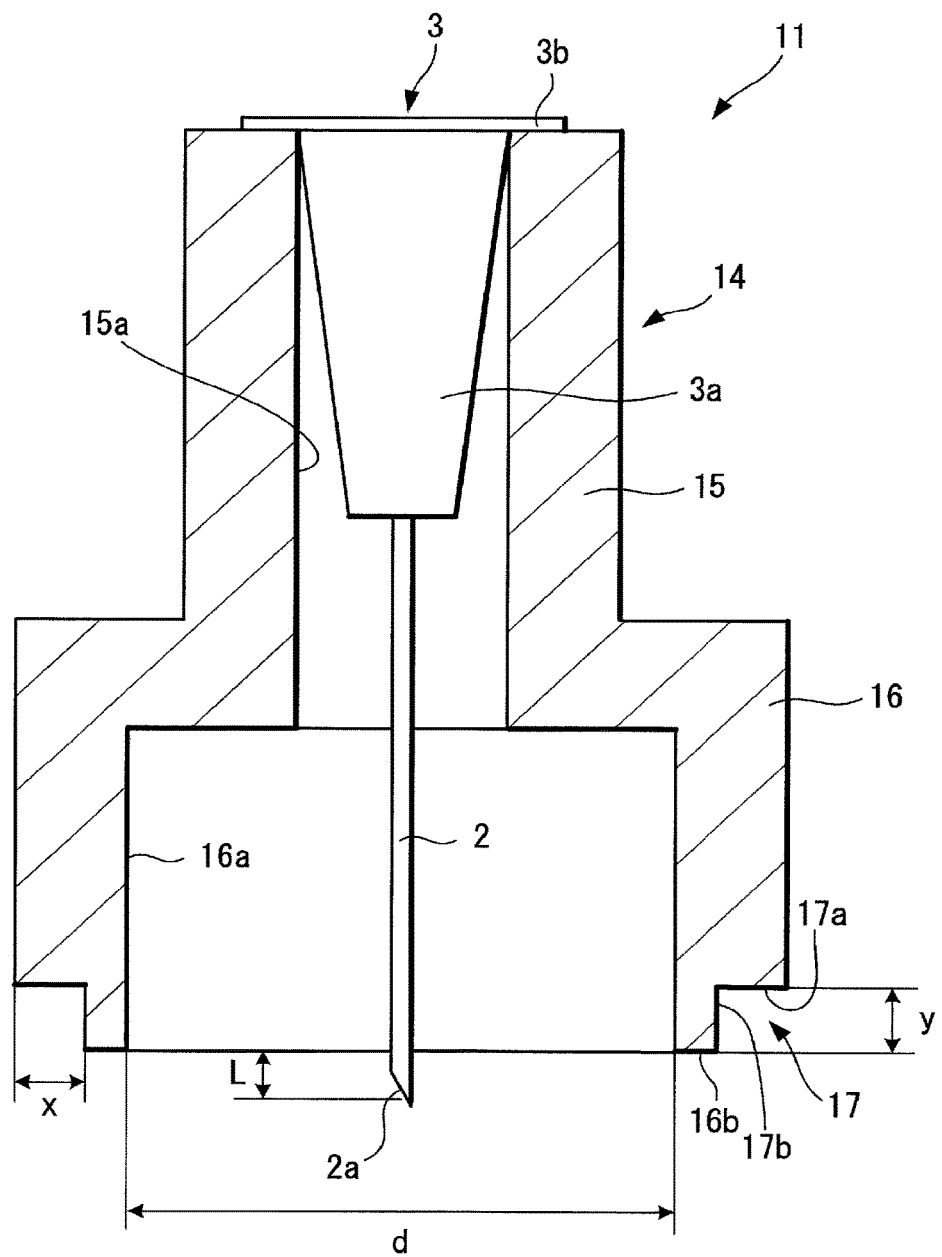
FIG. 10 is a view showing the configuration of an injection needle assembly according to a second embodiment of the present invention.

FIG. 10 is a view showing the configuration of the injection needle assembly according to the second embodiment of the present invention.

An injection needle assembly 11 has the same configuration as that of the injection needle assembly 1 of the first embodiment except for a stabilizer 14 and a guide portion 17. Thus, in the second embodiment, the description is made for the stabilizer 14 and the guide portion 17 only, and common components are denoted by common numerals as of the injection needle assembly 1 and the explanation thereof will be omitted.

Incidentally, the drug injection device of the present invention is formed by connecting a syringe 9 (see FIG. 3) with a hub 3 of the injection needle assembly 11.

The stabilizer (which is the skin deformer) 14 has a shape in which two circular tubes different in diameter are continuous in the axial direction. The stabilizer 14 includes a fixing portion 15 and a contact portion 16 continuously formed with fixing portion 15, the former forming one end portion of the stabilizer 14, and the latter forming the other end portion of the stabilizer 14. The material of the stabilizer 14 may be either a synthetic resin (plastic) such as polycarbonate, polypropylene, polyethylene or the like, or a metal such as stainless steel, aluminum or the like.

The fixing portion 15 of the stabilizer 14 has the same shape as that of the fixing portion 5 of the first embodiment, and is formed by a circular tube having a tube hole 15a. One end of the fixing portion 15 is fixed to a flange 3b of the hub 3 by a fixing means such as an adhesive. Further, the other end of the fixing portion 15 is continuous with the contact portion 16. Further, the hub body 3a of the hub 3 is housed in the tube hole 15a of the fixing portion 15.

The contact portion 16 of the stabilizer 14 is formed by a circular tube having a diameter larger than that of the fixing portion 15, and has a tube hole 16a communicating with the tube hole 15a of the fixing portion 15. The diameter of the tube hole 16a is larger than the diameter of the tube hole 15a of the fixing portion 15. A needle tube 2 held by the hub 3 is housed in the tube hole 16a of the contact portion 16. Further, the central line of the tube hole 16a coincides with the axis of the needle tube 2.

When puncturing the upper layer of skin with the needle tube 2, an end face 16b of the contact portion 16 is brought into contact with and pressed against the surface of the skin. When the end face 16b is pressed against the skin, a raised portion of the skin is formed in the tube hole 16a of the contact portion 16. Further, the needle tube 2 is stuck into the raised portion of the skin formed in the tube hole 16a.

The guide portion (which is the distance recognizer) 17 is provided at the end portion of the contact portion 16. The guide portion 17 is formed by cutting the end face 16b of the contact portion 16 to form a stepped portion, and has a contact surface 17a and a wall surface 17b.

The contact surface 17a of the guide portion 17 is a flat surface parallel to the end face 16b of the contact portion 16, and is formed in a circular ring shape continuing in the circumferential direction of the contact portion 16. The distance between the contact surface 17a and the end face 16b of the contact portion 16 corresponds to the "guide portion height y" of the first embodiment. Further, the wall surface 17b is a curved surface continuously extending in the circumferential direction of the contact portion 16. The distance between the wall surface 17b and the outer circumferential surface of the contact portion 16 corresponds to the "guide portion length x" of the first embodiment. In other words, the length of the contact surface 17a in the direction perpendicular to the outer circumferential surface of the contact portion 16 corresponds to the "guide portion length x".

With the injection needle assembly 11 having such configuration, the same functions and advantages as those of the injection needle assembly 1 of the aforesaid first embodiment can also be achieved. Specifically, by pressing the contact portion 16 until the contact surface 17a of the guide portion 17 contacts the skin, the press-in distance of the contact portion 16 to the skin can always be made constant.

As a result, the height of the raised portion of the skin formed in the tube hole 16a of the contact portion 16 can be made substantially constant. The insertion depth of the needle tube 2 into the skin is equal to the sum of the height of the raised portion of the skin and the distance from the end face 16b of the contact portion 16 to the needle tip of the needle tube 2. Thus, by making the height of the raised portion of the skin substantially constant, the insertion depth of the needle tube 2 into the skin can be made substantially constant.

3. Third Embodiment

Configuration Examples of Injection Needle Assembly and Drug Injection Device An injection needle assembly and a drug injection device according to a third embodiment of the present invention will be described below with reference to FIG. 11.

Figure 11:
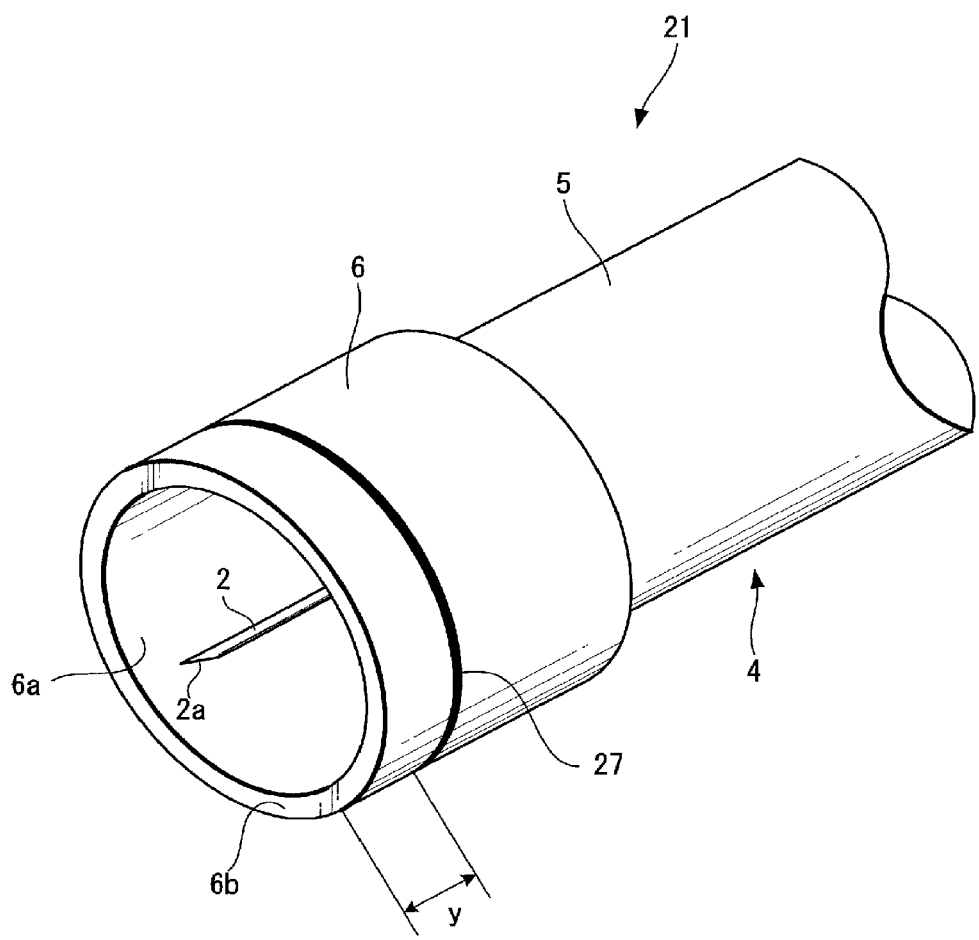
FIG. 11 is a perspective view showing an injection needle assembly according to a third embodiment of the present invention.

FIG. 11 is a perspective view showing the injection needle assembly according to the third embodiment of the present invention.

An injection needle assembly 21 has the same configuration as that of the injection needle assembly 1 of the first embodiment except for a guide portion (as the distance recognizer) 27. Thus, in the third embodiment, the description is made for the stabilizer 27 only, and common components are denoted by common numerals as of the injection needle assembly 1 and the explanation thereof will be omitted.

Incidentally, the injection needle assembly 21 has a hub 3 (see FIG. 1) identical to that provided in the first embodiment. Further, the drug injection device of the present invention is configured by connecting a syringe 9 (see FIG. 3) with the hub 3 of the injection needle assembly 21.

The guide portion 27 of the injection needle assembly 21 is a scale marked on a contact portion 6. The guide portion 27 is formed on the contact portion 6 by printing or painting. Incidentally, the printing or painting may be applied either on the outer circumferential surface of the contact portion 6, or on the inner circumferential surface of the contact portion 6. The guide portion 27 is continuously formed in the circumferential direction of the contact portion 6, and therefore can be recognized from any direction. The distance between the guide portion 27 and the end face 6b of the contact portion 6 corresponds to the "guide portion height y" of the first embodiment.

With the injection needle assembly 21 having such a configuration, the same functions and advantages as those of the injection needle assembly 1 of the aforesaid first embodiment can also be achieved. Specifically, by pressing the contact portion 6 until the guide portion (the scale) 27 is aligned with the surface of the skin around the contact portion 6, the press-in distance of the contact portion 6 to the skin can always be made constant.

As a result, the height of the raised portion of the skin formed in the tube hole 6a of the contact portion 6 can be made substantially constant. The insertion depth of the needle tube 2 into the skin is equal to the sum of the height of the raised portion of the skin formed in the tube hole 6a and the distance from the end face 6b of the contact portion 6 to the needle tip of the needle tube 2. Thus, by making the height of the raised portion of the skin substantially constant, the insertion depth of the needle tube 2 into the skin can be made substantially constant.

Although the guide portion 27 is formed on the contact portion 6 by printing or painting in the present embodiment, the guide portion 27 may also be formed by other methods. For example, the guide portion 27 may alternatively be provided by forming a groove in the contact portion 6, or by attaching a sheet on the contact portion 6.

Although only one guide portion (scale) 27, as the distance recognizer, is provided in the present embodiment, the injection needle assembly according to the present invention may be provided with two or more distance recognizers (scales). For example, the injection needle assembly may be provided with a distance recognizer (scale) for adults, and a distance recognizer (scale) for children. In such case, the guide portion height y of the distance recognizer for adults is higher (greater) than the guide portion height y of the distance recognizer for children, and the insertion depth of the needle tube 2 into the upper layer of skin of the adults is deeper than the insertion depth of the needle tube 2 into the upper layer of skin of the children. Thus, the insertion depth of the needle tube 2 into the upper layer of skin can be changed according to the thickness of the upper layer of skin, and therefore the needle tip of the needle tube 2 can be securely positioned in the upper layer of skin.

4. Fourth Embodiment

Configuration Examples of Injection Needle Assembly and Drug Injection Device An injection needle assembly and a drug injection device according to a fourth embodiment (referred to as "the present embodiment" hereinafter) of the present invention will be described below with reference to FIGS. 12 to 14. Incidentally, in the present embodiment, description for the parts identical to those of the first, second and third embodiments will be omitted.

Figure 12:
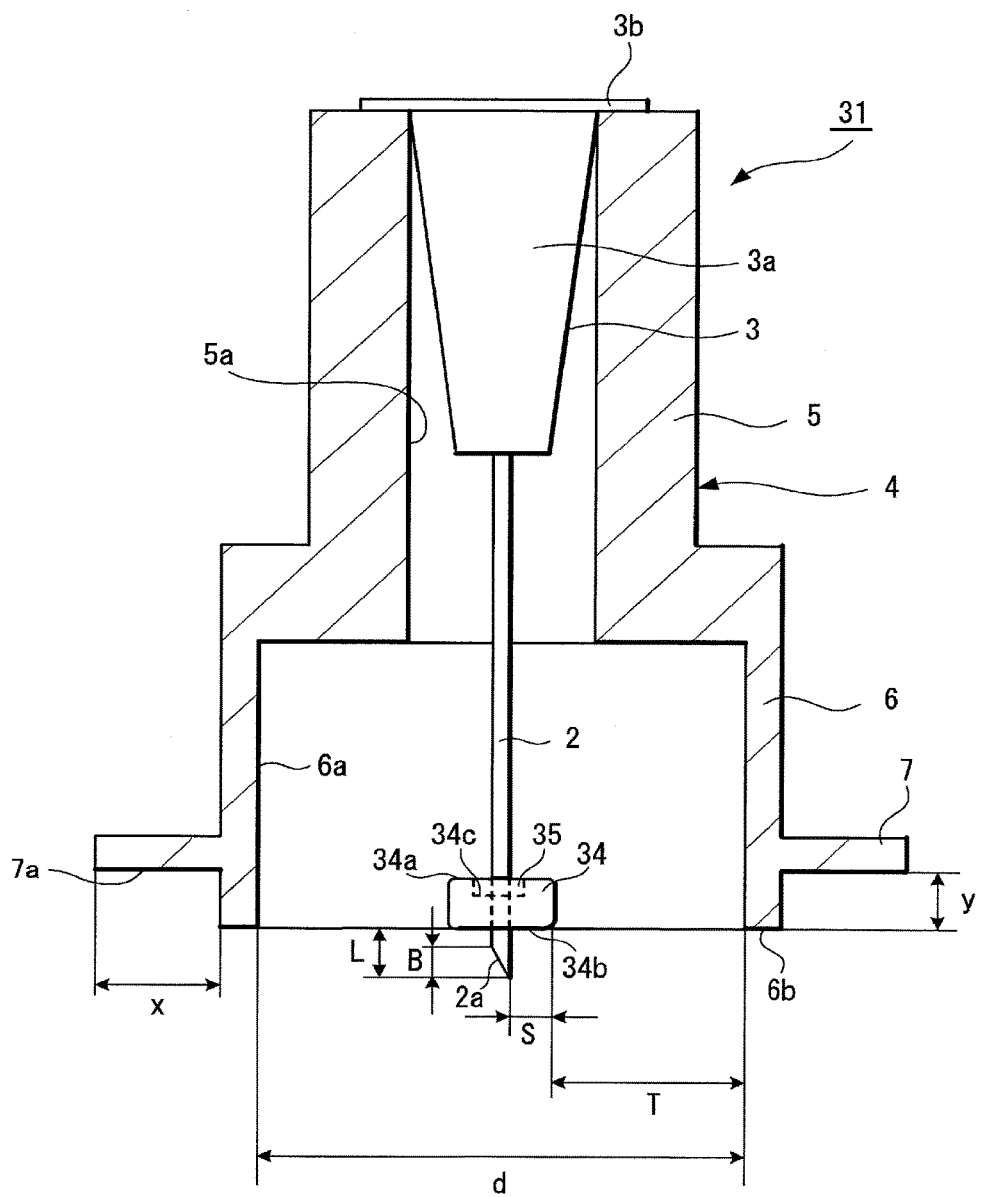
FIG. 12 is a view showing the configuration of an injection needle assembly according to a fourth embodiment of the present invention.
Figure 13:
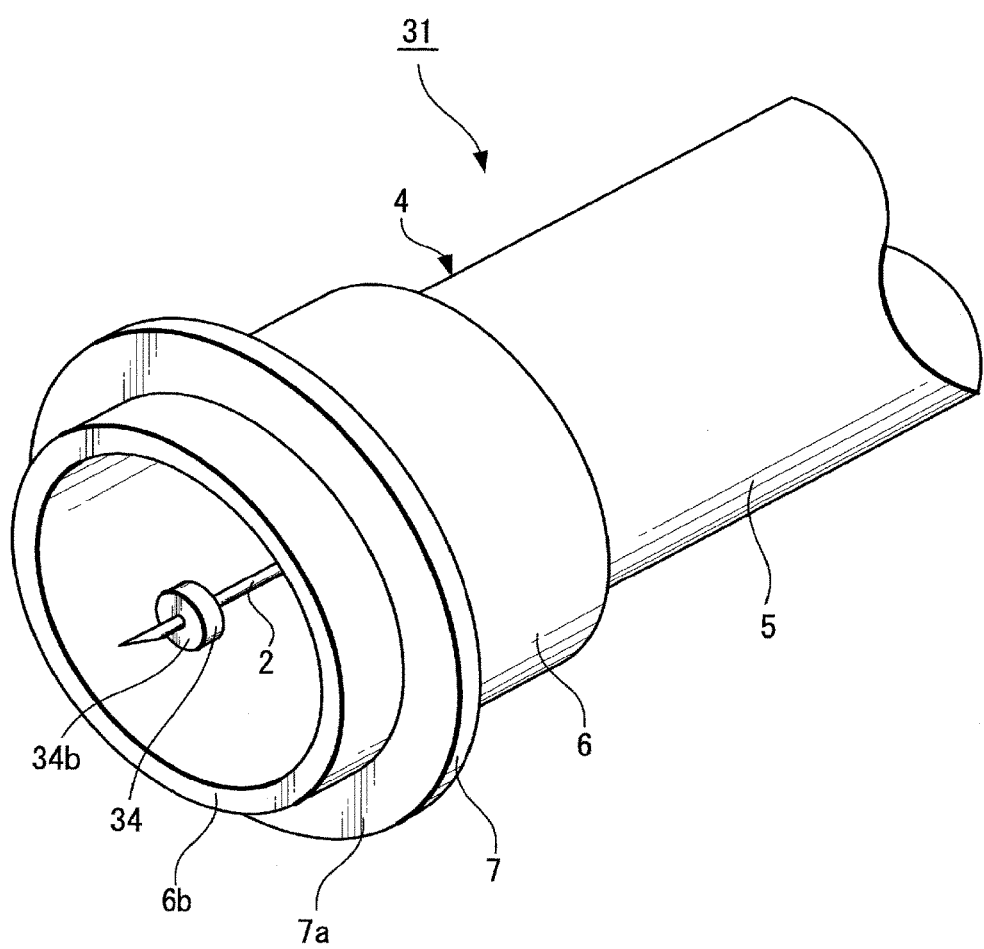
FIG. 13 is a perspective view showing the injection needle assembly according to the fourth embodiment of the present invention.

FIG. 12 is a schematic illustration showing the injection needle assembly according to the present embodiment, and FIG. 13 is a perspective view showing the injection needle assembly according to the present embodiment. FIG. 14 is a view for explaining a usage state of the drug injection device according to the present embodiment.

As shown in FIGS. 12 and 13, an injection needle assembly includes a hollow needle tube 2, a hub 3 which holds the needle tube 2, an adjusting portion 34 fixed to the needle tube 2, and a stabilizer 4. Further, a drug injection device of the present invention is configured by connecting a syringe 9 with the hub 3 (see FIG. 14).

The needle tube 2 may be a straight needle, a tapered needle in which at least a portion thereof is tapered, or the like. The tapered needle may have a configuration in which the external diameter of a base end portion fixed to the hub 3 is larger than the external diameter of a tip end portion including the needle tip, and a middle portion is tapered. Further, by arranging the adjusting portion in the tapered portion, the adjusting portion 34 is prevented from being moved toward the base end owing to the presence of the slope of the tapered portion. With such arrangement, even if the needle-protruding surface is strongly pressed against the skin, the length that the needle tip protrudes from the needle-protruding surface will never change, and therefore the needle can be securely stuck into a predetermined depth of the skin.

The tube hole of the needle tube 2 is communicated with the hub 3. The hub 3 includes a hub body 3a which holds the needle tube 2, and a flange 3b formed continuously from the hub body 3a. The hub body 3a has a tapered structure whose diameter becomes smaller gradually toward the tip end thereof. The base end portion of the needle tube 2 is fixed to the tip end portion of the hub body 3a. The flange 3b is formed in the base end portion of the hub body 3a. A stabilizer 4 is fixed to the flange 3b. The hub 3 may be in any form as long as it can be connected with the syringe.

The adjusting portion 34 is formed in a cylindrical shape. The needle tube 2 is passed through the adjusting portion 34, and the axis of the needle tube 2 and the axis of the adjusting portion 34 coincide with each other. The adjusting portion 34 is fixed in close contact with the circumferential surface of the needle tube 2. One end face of the adjusting portion 34 forms a hub-opposing surface 34a opposing the hub 3 and the other end face of the adjusting portion 34 forms a flat needle-protruding surface 34b from which the needle tip of the needle tube 2 protrudes.

In the hub-opposing surface 34a of the adjusting portion 34, a recess-for-adhesive 34c is provided so as to surround the circumference of the needle tube 2. The adjusting portion 34 is fixed in close contact with the circumferential surface of the needle tube 2 by applying an adhesive 35 in the recess-for-adhesive 34c in the state where the needle tube 2 has been penetrated through. Examples of the adhesive 35 include cyanoacrylate resin, epoxy resin, light curing resin and the like. However, materials prepared by other resins may also be employed as the adhesive 35.

When puncturing the upper layer of skin with the needle tube 2, the needle-protruding surface 34b of the adjusting portion 34 is brought into contact with the surface of skin, and thereby the insertion depth of the needle tube 2 is defined. In other words, the insertion depth of the needle tube 2 into the skin is determined by the protruding length of the needle tube 2 from the needle-protruding surface 34b (referred to as "needle-protruding length L" hereinafter).

As has been described above, the thickness of the upper layer of skin corresponds to the depth from the skin surface to the dermis layer, which is generally in a range of 0.5-3.0 mm. Therefore, the needle-protruding length L of the needle tube 2 can be set in a range of 0.5-3.0 mm. Consequently, in an injection into the upper layer of skin overlying the deltoid muscle, the preferable needle-protruding length L of the needle tube 2 can be set in a range of 0.9-1.4 mm.

Further, by setting the needle tube 2 in this manner, it becomes possible to securely position a blade face 2a in the upper layer of skin. As a result, the drug solution outlet opening in the blade face 2a can be positioned in the upper layer of skin, regardless of its position in the blade face 2a. Incidentally, even when the drug solution outlet is positioned in the upper layer of skin, if the needle tip is inserted into a depth deeper than the upper layer of skin, the drug solution will flow out from the upper layer of skin from between the side faces of the end portion of the needle tip and the incised skin. Thus, it is important that the needle tip and blade face of the needle tube 2 are securely positioned in the upper layer of skin.

Incidentally, in the case of a needle tube larger than 26 G, it is difficult to make the bevel length B 1.0 mm or less. Accordingly, to set the needle-protruding length L of the needle tube 2 in the preferable range (0.9-1.4 mm), it is preferred to use a needle tube smaller than 26 G.

The needle-protruding surface 34b of the adjusting portion 34 is formed such that the distance S from the circumferential edge of the needle-protruding surface 34b to the circumferential surface of the needle tube 2 is 1.4 mm or less, preferably in a range of 0.3-1.4 mm. The distance S from the circumferential edge of the needle-protruding surface 34b to the circumferential surface of the needle tube 2 is set by considering that the needle-protruding surface 34b presses the skin around the needle tube 2 to apply pressure to the blister formed in the upper layer of skin. Thus, even if the needle-protruding surface presses the skin around the needle tube, the administered drug can be prevented from being leaked out.

A synthetic resin (plastic) such as polycarbonate, polypropylene, polyethylene or the like may be used as the material of the adjusting portion 34, and a metal such as stainless steel, aluminum or the like may also be used as the material of the adjusting portion 34.

The adjusting portion 34 is fixed to the needle tube 2 using the adhesive 35 in the present embodiment. However, in the injection needle assembly according to the present invention, the adjusting portion may also be fixed to the needle tube 2 by other methods.

For example, in the case where the adjusting portion 34 is formed of a metal and is fixed to the needle tube 2, the aforesaid other methods may include swaging, welding and the like. Further, in the case where the adjusting portion 34 is formed of a synthetic resin and is fixed to the needle tube 2, the aforesaid other methods may include fusion, integral molding (especially, insert molding) and the like.

A contact portion 6 is arranged, by fixing a fixing portion 5 to the hub 3, so as to cover the circumference of the needle tube 2 and the adjusting portion 34. Incidentally, in the present embodiment, an end face 6b at one end side in the axial direction of the contact portion 6 is substantially flush with the needle-protruding surface 34b of the adjusting portion 34. Further, the needle tube 2 is perpendicular to the plane formed by the end face 6b of the stabilizer 4 and the needle-protruding surface 34b of the adjusting portion 34.

Figure 14:
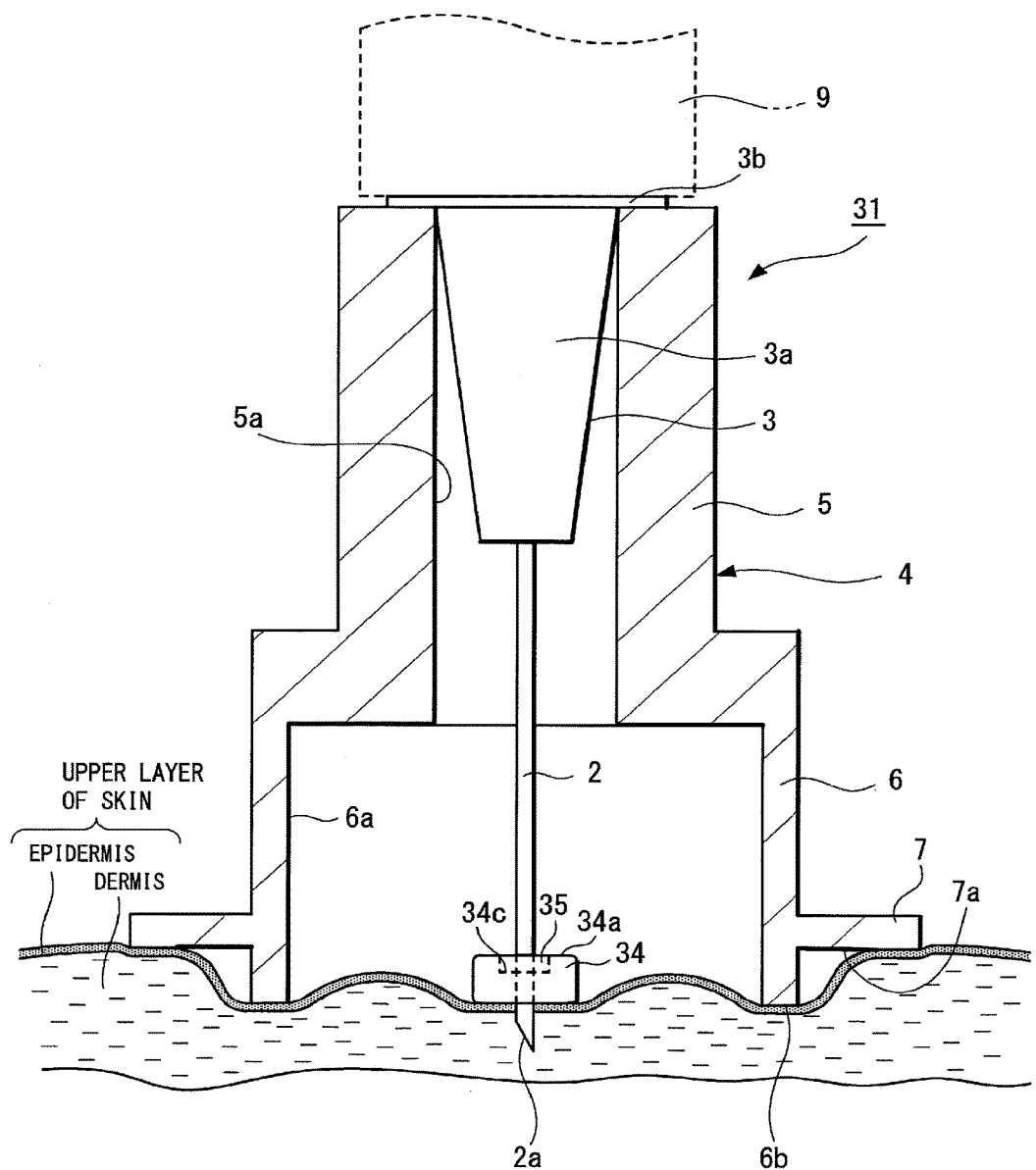
FIG. 14 is a view for explaining a state in which a needle tube of a drug injection device according to the fourth embodiment of the present invention is stuck into the skin.

Thus, as shown in FIG. 14, when sticking the needle tube 2 into the living body, the needle-protruding surface 34b of the adjusting portion 34 is brought into contact with the skin surface, and the end face 6b of the stabilizer 4 is also brought into contact with the skin surface. Thereby, the needle tube 2 can be supported by the stabilizer 4 substantially perpendicularly to the skin. As a result, the needle tube 2 can be prevented from waggling, and therefore the needle tube 2 can be stuck into the skin straight.

Incidentally, the needle-protruding surface 34b of the adjusting portion 34 does not have to be flush with the end face 6b of the stabilizer 4. In other words, the objects of the present invention may also be achieved when the needle-protruding surface 34b of the adjusting portion 34 is located on the other side in the axial direction of the stabilizer 4 from the end face 6*b* (i.e., on the side of the fixing portion 5). Further, considering the raised portion of the skin formed when the stabilizer 4 is pressed against the skin, it is preferred that the distance between the needle-protruding surface 34*b* of the adjusting portion 34 and the end face 6*b* in the axial direction is set to 1.3 mm or less.

Further, the internal diameter d of the contact portion 6 of the stabilizer 4 is set to a value equal to or larger than the diameter of the blister formed in the skin. To be specific, the distance T between the inner wall of the contact portion 6 and the outer circumferential surface of the adjusting portion 34 is set in a range of 4-15 mm. Thus, it can be prevented that a pressure is applied from the inner wall of the stabilizer 4 to the blister and the formation of the blister is obstructed.

Incidentally, the distance T between the inner wall of the stabilizer 4 and the outer circumferential surface of the adjusting portion 34 is set to 4 mm or more, but no particular upper limit is set for the distance T. However, if the distance T is too large, both the external diameter of the stabilizer 4 and the external diameter of the contact portion 6 will become large. If the external diameter of the contact portion 6 is large, it will be difficult to bring the end face 6*b* of the contact portion 6 into contact with the skin when the needle tube 2 is to be stuck into the skin of the slender arms of children. Thus, considering the slender arms of children, it is preferred that the distance T between the inner wall of the stabilizer 4 (the contact portion 6) and the outer circumferential surface of the adjusting portion 34 is defined to 15 mm as the maximum.

Further, if the distance S between the circumferential edge of the needle-protruding surface 34*b* of the adjusting portion 34 and the circumferential surface of the needle tube 2 is 0.3 mm or more, the adjusting portion 34 will not be penetrated through the skin. Thus, considering the diameter (about 0.3 mm) of the needle tube 2 and the distance T (4 mm or more) between the inner wall of the contact portion 6 and the outer circumferential surface of the adjusting portion 34, the internal diameter d of the contact portion 6 can be set to 9 mm or greater.

Further, a guide portion 7 is formed integrally with the outer circumferential surface of the contact portion 6 of the stabilizer 4. By pressing the stabilizer 4 until a contact surface 7*a* of the guide portion 7 contacts the skin, the force applied from both the stabilizer 4 and the needle tube 2 for pressing the skin can be constantly maintained at or above a predetermined value, and thereby the protruded portion of the needle tube 2 from the needle-protruding surface 34*b* (corresponding to the needle-protruding length L) can be securely inserted into the skin.

Further, the length of the distance (the guide portion height) y between the contact surface 7*a* of the guide portion 7 and the end face 6*b* of the stabilizer 4 is set so that the skin can be punctured by a suitable pressing force applied from the needle tube 2 and the stabilizer 4. Incidentally, the suitable pressing force applied from the needle tube 2 and the stabilizer 4 is in a range of, for example, 0.5-20 N. As a result, the pressing force applied from the needle tube 2 and the stabilizer 4 to the skin can be guided to the user by the guide portion 7, and the needle tip and blade face 2*a* of the needle tube can be securely positioned in the upper layer of skin, thereby giving the user a sense of reassurance.

Specifically, in the case where the internal diameter d of the stabilizer 4 is set in a range of 12-14 mm, the guide portion height y is calculated using the following Expression 1, based on the length (the guide portion length) x between the protruding end face of the guide portion 7 and the outer circumferential surface of the stabilizer 4.

$$1.0\ \text{Ln}(x)+1.2<y<3.1\ \text{Ln}(x)+3.2 \qquad \text{[Expression 1]}$$

Expression 1 was determined based on the results of experimental examples described later.

Incidentally, in the case where the internal diameter d of the stabilizer 4 is 11 mm, the guide portion height y is set in a range of 0.75-2.6 mm when the guide portion length x is 0.5 mm, for example. Similar to Expression 1, this value was determined based on the results of experimental examples described later.

Incidentally, the shape of the stabilizer 4 is not limited to the circular tube shape, and may also be formed, for example, in a polygonal prism shape, such as a quadrangular prism shape, a hexagonal prism shape or the like, having a tube hole formed in the center thereof. Further, the stabilizer may also have a configuration in which the fixing portion 5 and the contact portion 6 have the same diameter.

Further, although the present embodiment is described based on an example in which the stabilizer 4 is fixed to the hub 3, the stabilizer 4 may also be fixed to the syringe 9 which constitutes the drug injection device. Further, although the stabilizer 4 is fixed to the hub 3 using an adhesive in the present embodiment, the injection needle assembly according to the present invention may have a configuration in which the stabilizer 4 is fixed to the hub 3 by other methods. For example, in the case where the stabilizer 4 is made of a metal and is fixed to the hub 3, the aforesaid other methods may include swaging, welding and the like. Further, in the case where the stabilizer 4 is made of a synthetic resin and is fixed to the hub 3, the aforesaid other methods may include fusion, integral molding (especially, insert molding) and the like.

Method of Using Drug Injection Device

Next, a method of using the drug injection device to which the injection needle assembly 31 is applied will be described below with reference to FIG. 14.

First, the end face 6*b* of the stabilizer 4 is caused to face the skin, and thereby the needle tip of the needle tube 2 is caused to face the skin to be punctured. Next, the injection needle assembly 31 is moved substantially perpendicular to the skin, and the needle tube 2 is stuck into the skin while the end face 6*b* of the stabilizer 4 is pressed against the skin. Here, the needle-protruding surface 34*b* of the adjusting portion 34 is flush with the end face 6*b* of the stabilizer 4. Thereby, the needle-protruding surface 34*b* of the adjusting portion 34 can contact the skin to flatly deform the skin, and the needle tube 2 can be inserted into the skin by the needle-protruding length L only.

Next, the stabilizer 4 is pressed until the contact surface 7*a* of the guide portion 7 is brought into contact with the skin. Here, the value of the guide portion height y is set so as to puncture the skin with a suitable pressing force of the needle tube 2 and the stabilizer 4 can. Thus, the force of the stabilizer 4 for pressing against the skin becomes a predetermined value. Thus, the pressing force of the stabilizer 4 can be guided to the user; the stabilizer 4 can be pressed against the skin by the suitable pressing force; and the needle tip and the blade face 2*a* of the needle tube 2 can be securely positioned in the upper layer of skin. In such a manner, since the guide portion 7 serves as a mark for guiding the pressing force of the stabilizer 4, the needle tip of the needle tube can be securely positioned in the upper layer of skin, so that the drug can be securely administered into the upper layer of skin, and therefore it is possible to bring the user more sense of reassurance. Here, the pressing force for pressing the stabilizer 4 until the guide portion 7 is brought into the contact with the skin is defined as a pressing parameter when puncturing the skin.

Further, by abutting the stabilizer 4 against the skin, the needle tube 2 is stabilized, and the needle tube 2 can puncture the skin straight. Thus, the waggling caused in the needle tube 2 can be prevented, and the drug can be administered stably. When using a needle with a very short protruding length of about 0.5 mm, for example, there is a case that the needle will not be inserted into the skin even if the needle tip is brought into contact with the skin. However, when the stabilizer 4 is pressed against the skin and the skin is pressed down perpendicularly, the skin inside the stabilizer 4 is strained so as to be in a tensioned state. Thus, since the skin becomes hard to flee from the needle tip of the needle tube 2, the stabilizer 4 has an effect of making it easier for the needle tip to puncture the skin.

Further, since the needle-protruding length L is set in the range of 0.5-3.0 mm, the needle tip and the blade face 2a of the needle tube 2 is securely positioned in the upper layer of skin. Thereafter, the drug is injected into the upper layer of skin using the syringe 9 connected with the hub 3.

The adjusting portion 34 of the injection needle assembly is fixed in close contact with the circumference of the needle tube 2, and no gap is formed between the adjusting portion 34 and the portion of the needle tube 2 penetrating through the adjusting portion 34. Thus, if the needle-protruding surface 34b of the adjusting portion 34 is brought into contact with the skin, the skin around the needle tube 2 can be flatly deformed. As a result, the needle tube 2 can be inserted into the skin by the needle-protruding length L only, and the needle tip of the needle tube 2 can be securely positioned in the upper layer of skin.

Further, since the size of the needle-protruding surface 34b of the adjusting portion 34 and the internal diameter d of the stabilizer 4 are set to suitable values, the administered drug can be prevented from leaking out from the body, and therefore the drug can be securely administered in the upper layer of skin.

Experimental Examples

Next, experimental examples in which the press-in distance of the stabilizer 4 to the skin (corresponding to the guide portion height y) when the stabilizer 4 was pressed against the skin by a predetermined pressing force was measured will be described below with reference to FIGS. 15A to 17.

Figure 15A:
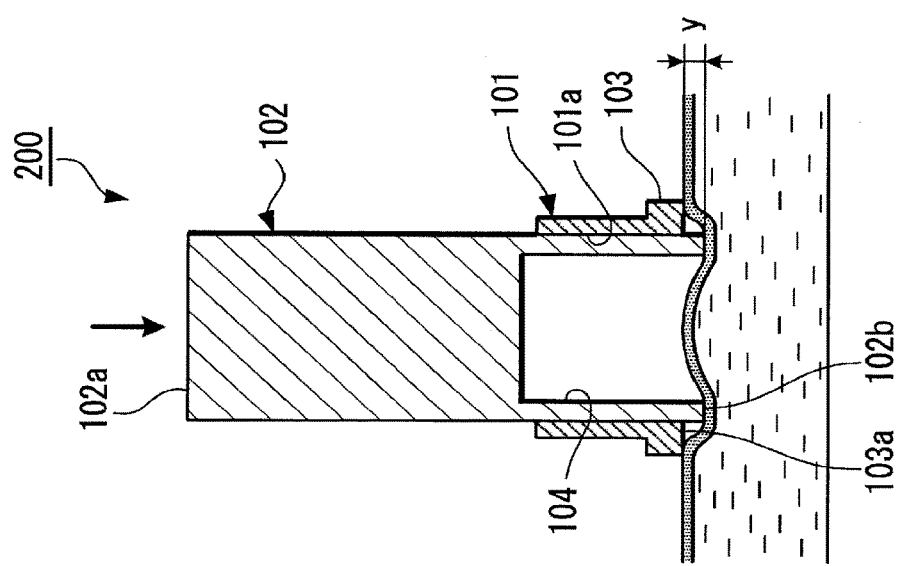
FIGS. 15A and 15B are views showing a measuring device for measuring a guide portion height of the drug injection device according to the fourth embodiment of the present invention, where
Figure 15B:
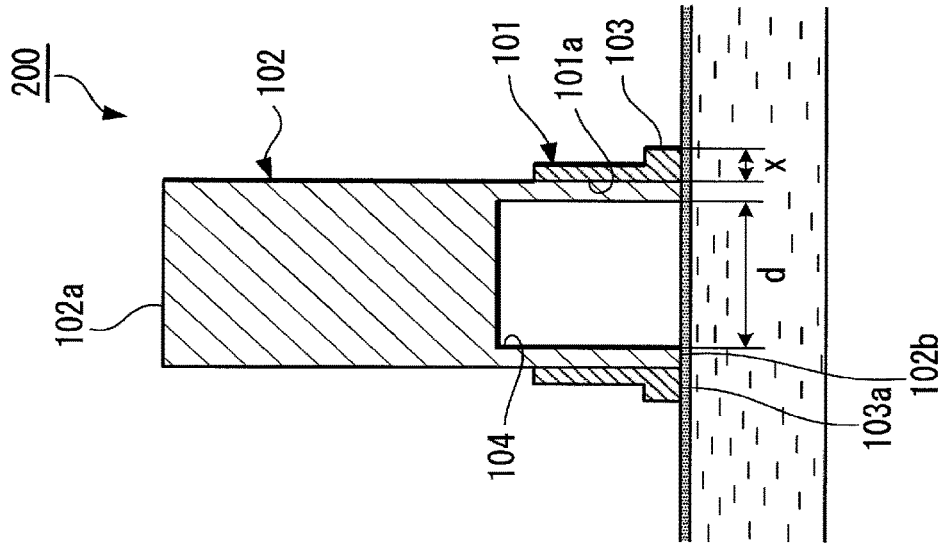
Figure 16:
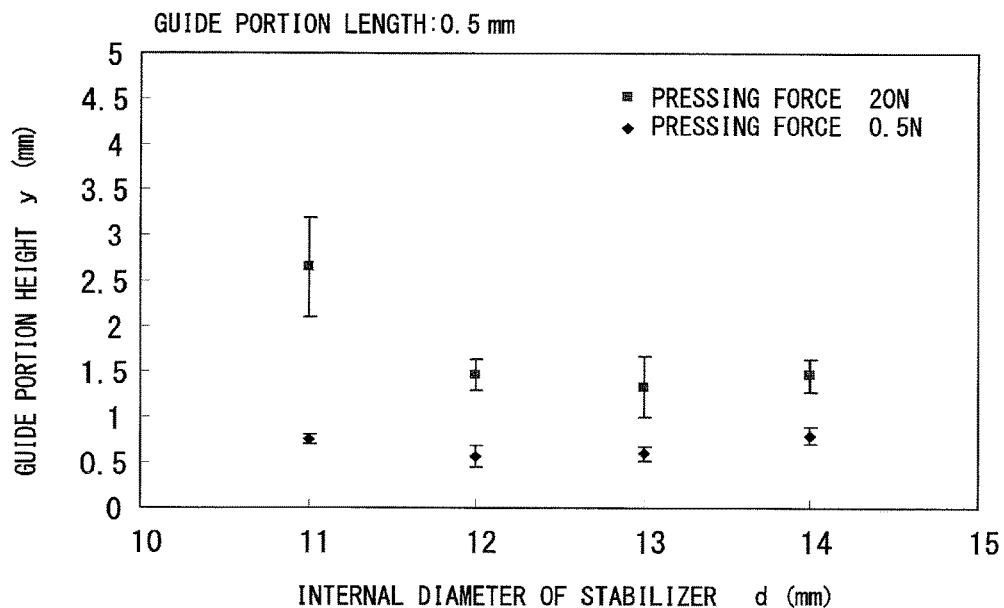
FIG. 16 is a graph showing the measured values of the guide portion height obtained by varying the internal diameter of a contact portion.
Figure 17:
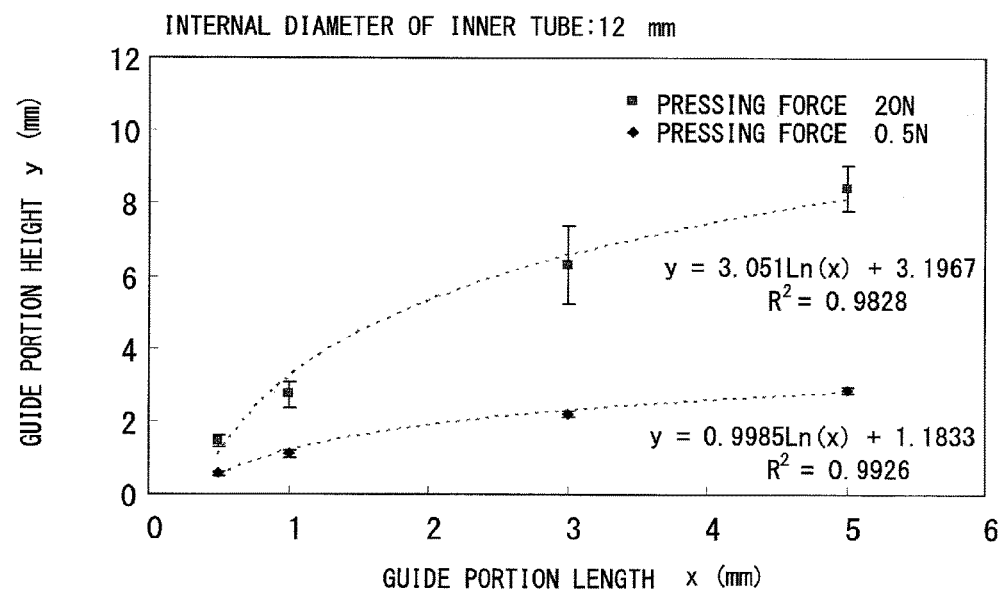
FIG. 17 is a graph showing the measured values of the guide portion height obtained by varying guide portion length.

FIGS. 15A and 15B are views showing a measuring device for measuring the guide portion height y. FIG. 16 is a graph showing the measured values of the guide portion height y obtained by varying the internal diameter d of the contact portion 6. FIG. 17 is a graph showing the measured values of the guide portion height y obtained by varying the guide portion length x.

First, a measuring device 200 used in this experiment will be described below. The measuring device 200 is formed by cutting a synthetic resin (plastic). The measuring device 200 includes an outer tube 101 formed in a circular tube shape, and a pressing member 102 fitted into the tube hole 101a of the outer tube 101 slidably.

A flange 103 projecting in the radial direction of the outer tube 101 is provided to one end portion (a lower end portion) of the outer tube 101. A bottom surface 103a of the flange 103 is coplanar with an end face of the outer tube 101. The flange 103 corresponds to the guide portion 7 of the injection needle assembly 31 (see FIG. 12). Further, the thickness of the outer tube 101 including the flange 103 in the radial direction corresponds to the guide portion length x of the injection needle assembly 31.

The pressing member 102 is formed by a cylinder having substantially the same diameter as the diameter of the tube hole 101a of the outer tube 101, and has an upper surface 102a and a bottom surface 102b. A circular recess 104 is formed in the bottom surface 102b of the pressing member 102. The diameter of the recess 104 corresponds to the internal diameter d of the contact portion 6 of the stabilizer 4 of the injection needle assembly 31.

On the other hand, due to the provision of the recess 104, the bottom surface 102b of the pressing member 102 is formed in a circular ring shape. The bottom surface 102b of the pressing member 102 corresponds to the end face 6b of the stabilizer 4 of the injection needle assembly 31. Incidentally, in the measuring device 200 used in the present experiment, the width of the bottom surface 102b of the pressing member 102 is set to 0.5 mm.

To measure the guide portion height y using the measuring device 200 having the aforesaid configuration, first the measuring device 200 is mounted on the skin as shown in FIG. 15A. At this time, the bottom surface 103a of the flange 103 provided to the outer tube 101 and the bottom surface 102b of the pressing member 102 are brought into contact with the skin.

Next, as shown in FIG. 15B, the upper surface 102a of the pressing member 102 is pressed with a predetermined force, and thereby the pressing member 102 is moved relative to the tube hole 101a of the outer tube 101, so that the bottom surface 102b of the pressing member 102 is pressed against the skin. As a result, the outer tube 101 and the pressing member 102 are formed into the same configuration as the stabilizer 4 in the state where the contact portion 6 is pressed against the skin.

When the bottom surface 102b of the pressing member 102 is pressed against the skin, a raised portion of the skin is formed inside the recess 104. Further, the distance between the bottom surface 102b of the pressing member 102 and the bottom surface 103a of the flange 103 corresponds to the guide portion height y of the injection needle assembly 31. Thus, the guide portion height y can be set by measuring the distance between the bottom surface 102b of the pressing member 102 and the bottom surface 103a of the flange 103.

In the present experiment, the guide portion height y of the skin overlying the deltoid muscle, which is the administration site of vaccine, was measured for 10 adults. In the present experiment, first, the guide portion height y was measured by using four measuring devices 200, wherein the diameters of the recesses 104 (the internal diameter d of the contact portion 6) were 11 mm, 12 mm, 13 mm and 14 mm respectively. Incidentally, the guide portion length x was set to 0.5 mm. Further, the pressing forces for pressing the pressing member 102 were 0.5 N and 20 N. The pressing forces of 0.5 N and 20 N are respectively the minimum value and the maximum value of the pressing force in the practical use. The pressing forces of 0.5 N was the minimum value of the pressing force capable of puncturing the skin, and it was impossible to puncture the skin with a pressing forces of less than 0.5 N. The pressing force of 20 N is the maximum value of the pressing force capable of administering the drug into the upper layer of skin. If the pressing force is larger than 20 N, since the pressing force exerted on the adjusting portion 34 is too large, the skin will be pushed and deformed and the needle tip reaches a subcutaneous layer. Therefore it will be difficult to administer the drug into the upper layer of skin. By performing such a measurement, it is possible to confirm whether or not the guide portion height y varies with the variation of the internal diameter d of the contact portion 6. The experimental result is shown in FIG. 16.

As shown in FIG. 16, in the case where the internal diameter d of the contact portion 6 was 11 mm, when the pressing force was 0.5 N, the guide portion height y became about 0.75 mm. While when the pressing force was 20 N, the guide portion height y became about 2.6 mm. Thus, it is understood that, in the case where the internal diameter d of the contact portion 6 is 11 mm, when the guide portion length x is set to 0.5 mm and the guide portion height y is set in a range of 0.75-2.6 mm, the guide portion 7 functions as a guide when the injection needle assembly 31 is pressed against the skin by a pressing force of 0.5-20 N.

Further, in the case where the internal diameter d of the contact portion 6 was in a range of 12-14 mm, when the pressing force was 0.5 N, the guide portion height y was in a range of 0.6-0.8 mm. While when the pressing force was 20 N, the guide portion height y was in a range of 1.4-1.5 mm. Thus, it is understood that, in the case where the internal diameter d of the contact portion 6 is in the range of 12-14 mm, when the guide portion length x is set to 0.5 mm and the guide portion height y is set in a range of 0.6-1.5 mm, the guide portion 7 functions as a guide when the injection needle assembly 31 is pressed against the skin by a pressing force of 0.5-20 N.

Here, it is understood that, in the case where the internal diameter d of the contact portion 6 is in the range of 12-14 mm, the guide portion height y does not vary greatly. Next, the internal diameter d of the contact portion 6 is set to 12 mm, and the guide portion height y was measured by varying the guide portion length x in a range of 0.5-5 mm. The experimental result is shown in FIG. 17. Incidentally, the force for pressing the pressing member 102 was set in a range of 0.5-20 N, which is the same value as the experiment described above.

As shown in FIG. 17, when the guide portion length x was increased, the guide portion height y increased regularly. Thus, it is understood that the guide portion height y and the guide portion length x are in correlation with each other. In other words, it is understood that the guide portion height y is proportional to the guide portion length x. Further, based on the present experiment, the relation between the guide portion height y and the guide portion length x defined by Expression 1 was obtained.

$$1.0 \, \text{Ln}(x)+1.2 \leq y < 3.1 \, \text{Ln}(x)+3.2 \quad \text{[Expression 1]}$$

It is understood, based on the above experimental results, that the guide portion height y (see FIG. 14) can be determined by varying the guide portion length x. Incidentally, as described above, in the case where the internal diameter d of the contact portion 6 is in the range of 12-14 mm, the guide portion height y does not vary greatly. Thus, in the case where the internal diameter d of the contact portion 6 is in the range of 12-14 mm, the guide portion height y may be set to a value which satisfies the relation defined by Expression 1. Thereby, the guide portion 7 functions as a guide when the injection needle assembly 31 is pressed against the skin by a pressing force of 0.5-20 N, the needle tip and the blade face 2a of the needle tube 2 can be securely positioned in the upper layer of skin, and therefore it is possible to bring the user more sense of reassurance.

Incidentally, the pressing force for pressing the injection needle assembly 31 against the skin can be set in a range of 0.5-20 N. Such range of the pressing force is confirmed by performing an experiment in which a device having no guide portion 7 of the injection needle assembly 31 is used to administer a drug solution into a skin of a pig by a pressing force of 5-20 N, and the experimental result shows that it is possible to administer the drug solution into the dermis without leak.

5. Fifth Embodiment

Configuration Examples of Injection Needle Assembly and Drug Injection Device

Next, an injection needle assembly according to a fifth embodiment of the present invention will be described below with reference to FIG. 18.

Figure 18:
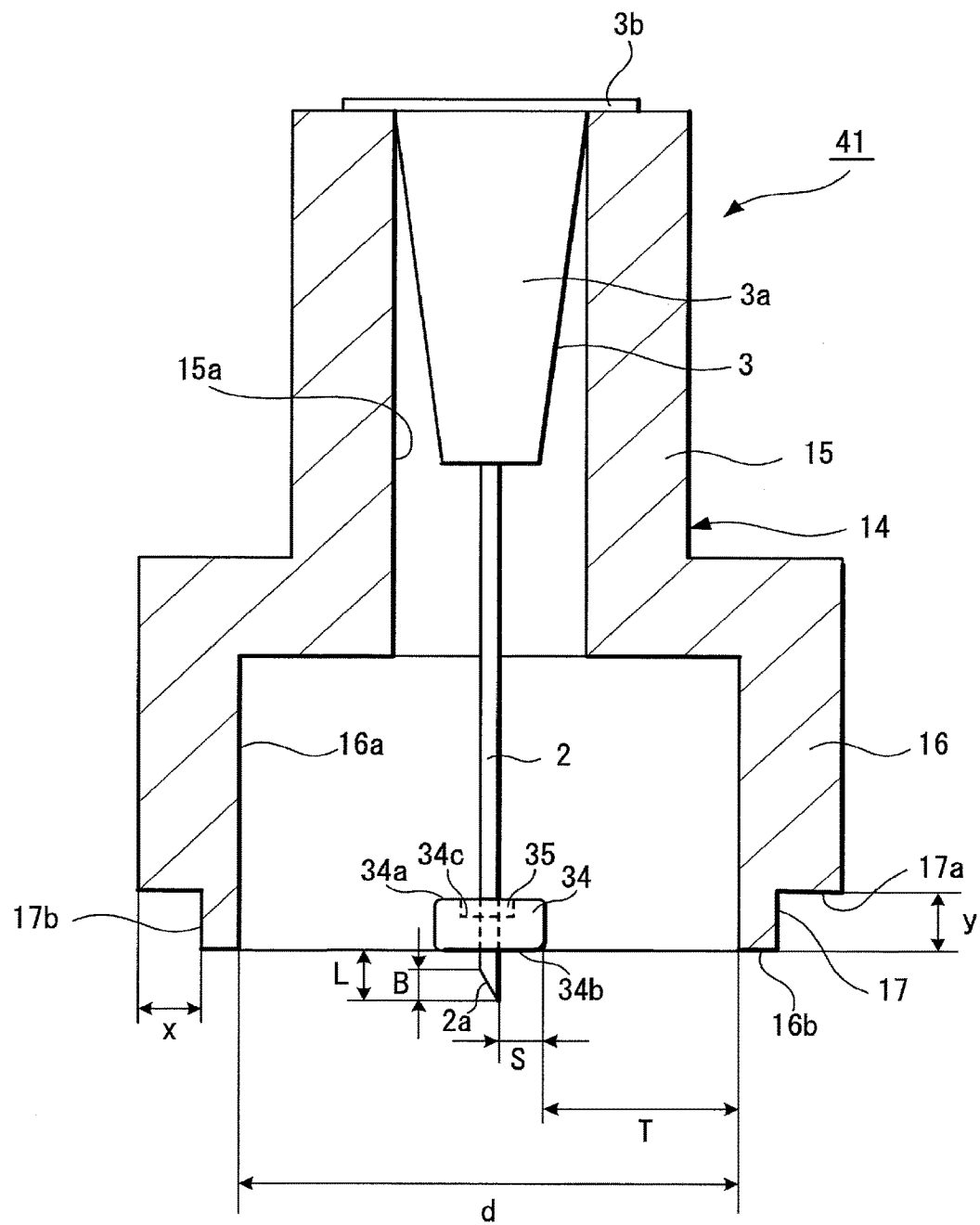
FIG. 18 is a view showing the configuration of an injection needle assembly according to a fifth embodiment of the present invention.

FIG. 18 is a cross section view showing the injection needle assembly according to the fifth embodiment.

An injection needle assembly 41 according to the fifth embodiment has the same configuration as that of the injection needle assembly 31 (see FIG. 12) of the fourth embodiment except for a stabilizer 14 and a guide portion 17. Further, the stabilizer 14 and the guide portion 17 are identical to those of the injection needle assembly 11 (see FIG. 10) of the second embodiment. Thus, in the present embodiment, common components are denoted by common numerals as of the injection needle assembly 11 and the injection needle assembly 31, and the explanation thereof will be omitted.

Similar to the fourth embodiment, the drug injection device of the present invention is configured by connecting a syringe with a hub 3 of the injection needle assembly 41.

A needle tube 2, the hub 3 and an adjusting portion 34 are arranged in the tube hole of the stabilizer 14. Further, the stabilizer 14 includes a fixing portion 15 fixed to the hub 3, and a contact portion 16 covering the circumference of the needle tube 2 and the adjusting portion 34. A hub body 3a of the hub 3 is housed in a tube hole 15a of the fixing portion 15. Further, the contact portion 16 is arranged, by fixing the fixing portion 15 to the hub 3, so as to cover the circumference of the needle tube 2 and the adjusting portion 34.

The guide portion 17 is continuously formed in the circumferential direction of the outer circumferential surface of the stabilizer 14, and is formed as a stepped portion recessed substantially perpendicularly from the outer circumferential surface of the stabilizer 14 to the inner side in the radial direction. The guide portion 17 is formed by continuously cutting the contact portion 16 of the stabilizer 14 in the circumferential direction to form the stepped portion, and has a contact surface 17a and a wall surface 17b. The contact surface 17a is a surface substantially parallel to an end face 16b of the stabilizer 14, and is brought into contact with the skin when the stabilizer 14 is pressed against the skin. The distance between the contact surface 17a and the end face 16b corresponds to the "guide portion height y" of the fourth embodiment. Further, the value of the guide portion height y is set so as to puncture the skin by applying a suitable pressing force of the needle tube 2 and the stabilizer 14.

Further, the wall surface 17b is a continuous curved surface substantially perpendicular to the contact surface 17a, and faces the same direction as the outer circumferential surface of the contact portion 16. The distance between the wall surface 17b and the outer circumferential surface of the contact portion 16 corresponds to the "guide portion length x" of the fourth embodiment.

Further, similar to the injection needle assembly 31 of the fourth embodiment, by pressing the stabilizer 14 until the contact surface 17*a* of the guide portion 17 contacts the skin, the forces of stabilizer 14 for pressing the skin can be constantly maintained at or above a predetermined value. As a result, the needle tip and the blade face of the needle tube can be securely positioned in the upper layer of skin. Thus, with the injection needle assembly 41, the same functions and advantages as those of the injection needle assembly 31 of the fourth embodiment can also be achieved.

It is to be understood that the injection needle assembly and the drug injection device according to the present invention is not limited to the embodiments described above, and various modifications and variations in material, configuration and the like can be made without departing from the constitution of the present invention.

Although the stabilizer 4 (14) is fixed to the hub 3 according to the first to fifth embodiments of the present invention, the stabilizer according to the present invention may also be, for example, fixed to the syringe constituting the drug injection device. Also, the stabilizer according to the present invention may also be integrally formed with the hub or the syringe.

EXPLANATION OF REFERENCE NUMERALS 1, 11, 21, 31, 41 injection needle assembly
2 needle tube
2*a* blade face 2*a*
3 hub
4, 14 stabilizer
5, 15 fixing portion
5*a*, 15*a* tube hole
6, 16 contact portion
6*a*, 16*a* tube hole
6*b*, 16*b* end face
7, 17, 27 guide portion (distance recognizer)
7*a*, 17*a* contact surface
9 syringe
34 adjusting portion
34*a* hub-opposing surface
34*b* needle-protruding surface
B bevel length
d internal diameter
L needle-protruding length
P insertion length
S distance from the circumferential edge of the needle-protruding surface to the circumferential surface of the needle tube
T distance from the inner wall of the stabilizer to the outer circumferential surface of the adjusting portion
x guide portion length (recognizer length)
y guide portion height (recognizer height)
z skin-raising length

The invention claimed is:

1. An injection needle assembly comprising:
a needle tube, smaller than 26 G in size, having a needle tip capable of puncturing a living body and a bevel length of 1.4 mm or shorter so as to be placed in a skin upper layer;
a hub for holding the needle tube;
a stabilizer formed in a tubular shape surrounding the circumference of the needle tube and having an end face that contacts a skin of the living body when puncturing the living body with the needle tube; and
a guide portion provided on the stabilizer for guiding, by being contacted with the skin, a pressing parameter applied from the needle tube and the stabilizer to the living body when puncturing the living body with the needle tube.

2. The injection needle assembly according to claim 1, wherein the stabilizer is a skin deformer adapted to form a raised portion of the skin in a tube hole thereof by pressing the end face of the stabilizer against the skin; wherein the pressing parameter is a press-in distance of the skin deformer to the skin; and wherein the guide portion is a distance recognizer adapted to recognize the press-in distance.

3. The injection needle assembly according to claim 2, wherein the distance recognizer is a stepped portion formed in an outer circumferential surface of the skin deformer.

4. The injection needle assembly according to claim 2, wherein the distance recognizer is a flange projecting from an outer circumferential surface of the skin deformer.

5. The injection needle assembly according to claim 3, wherein the distance recognizer has a contact surface parallel to the end face of the skin deformer, the contact surface being caused to recognize, by being brought into contact with the skin, the press-in distance of the skin deformer to the skin.

6. The injection needle assembly according to claim 5, wherein the contact surface of the distance recognizer is continuous with the outer circumferential surface of the skin deformer, and a recognizer length, which is a length of the contact surface of the distance recognizer in a direction perpendicular to the outer circumferential surface of the skin deformer, is in a range of 0.5-5.0 mm.

7. The injection needle assembly according to claim 6, wherein the tube hole of the skin deformer is formed in circular shape.

8. The injection needle assembly according to claim 7, wherein a diameter of the tube hole of the skin deformer is in a range of 8-28 mm.

9. The injection needle assembly according to claim 8, wherein the diameter of the tube hole of the skin deformer is in a range of 11-14 mm.

10. The injection needle assembly according to claim 9, wherein, in the case where the recognizer length is set in a range of 3.0-5.0 mm, if z represents the height of the raised portion of the skin and y represents the distance between the end face of the skin deformer and the distance recognizer, then z and y satisfy the relation defined by the following expression:

$$z=0.1y+0.1.$$

11. The injection needle assembly according to claim 1, further comprising an adjusting portion arranged around the needle tube, the adjusting portion having a needle-protruding surface from which the needle tip of the needle tube protrudes, wherein the pressing parameter is a pressing force.

12. The injection needle assembly according to claim 11, wherein the pressing force is in a range of 0.5-20 N.

13. The injection needle assembly according to claim 11, wherein the guide portion has a stepped portion formed in an outer circumferential surface of the stabilizer and substantially perpendicular to the outer circumferential surface of the stabilizer.

14. The injection needle assembly according to claim 11, wherein the guide portion is a flange projecting substantially perpendicularly from an outer circumferential surface of the stabilizer.

15. The injection needle assembly according to claim 13, wherein the stabilizer is formed in a circular tube shape.

16. The injection needle assembly according to claim 15, wherein, in the case where the internal diameter of the stabilizer is set in a range of 12-14 mm, if y represents the distance between a contact surface of the guide portion and the end face of the stabilizer, the contact surface and the end face contacting the skin, and x represents a guide portion length which is a length of the guide portion from the stabilizer in a substantially perpendicular direction, then y and x satisfy the relation defined by the following expression:

$$1.0\ \mathrm{Ln}(x)+1.2<y<3.1\ \mathrm{Ln}(x)+3.2.$$

17. The injection needle assembly according to claim 15, wherein, in the case where the internal diameter of the stabilizer is set to 11 mm, the distance between a contact surface of the guide portion and the end face of the stabilizer, the contact surface and the end face contacting the skin, is set in a range of 0.75-2.6 mm when a guide portion length which is a length of the guide portion from the stabilizer in a substantially perpendicular direction is 0.5 mm.

18. The injection needle assembly according to claim 11, wherein the needle-protruding surface of the adjusting portion is formed such that the distance from a circumferential edge of the needle-protruding surface to a circumferential surface of the needle tube is in a range of 0.3-1.4 mm.

19. The injection needle assembly according to claim 11, wherein a distance from an inner wall of the stabilizer to an outer circumferential surface of the adjusting portion is set in a range of 4-15 mm.

20. The injection needle assembly according to claim 1, wherein the guide portion projects radially from an outer circumferential surface of the stabilizer and contacts the skin at a contact surface which is parallel to the end face of the stabilizer.

21. A drug injection device comprising:
a needle tube, smaller than 26 G in size, having a needle tip capable of puncturing a living body and a bevel length of 1.4 mm or shorter so as to be placed in a skin upper layer;
a hub for holding the needle tube;
a syringe connected to the hub;
a stabilizer formed in a tubular shape surrounding the circumference of the needle tube and having an end face that contacts a skin of the living body when puncturing the living body with the needle tube; and
a guide portion provided on the stabilizer for guiding, by being contacted with the skin, a pressing parameter applied from the needle tube and the stabilizer to the living body when puncturing the living body with the needle tube.

22. The drug injection device according to claim 21, wherein the guide portion projects radially from an outer circumferential surface of the stabilizer and contacts the skin at a contact surface which is parallel to the end face of the stabilizer.

* * * * *